(12) United States Patent     (10) Patent No.: US 11,406,372 B2
Einarsson et al.     (45) Date of Patent: Aug. 9, 2022

(54) SYSTEMS AND METHODS FOR SUTURING TISSUE

(71) Applicant: The Brigham and Women's Hospital, Inc., Boston, MA (US)

(72) Inventors: Jon I. Einarsson, Boston, MA (US); Mobolaji Ajao, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 284 days.

(21) Appl. No.: 16/752,712

(22) Filed: Jan. 27, 2020

(65) Prior Publication Data

US 2020/0155142 A1     May 21, 2020

Related U.S. Application Data

(63) Continuation of application No. 16/368,495, filed on Mar. 28, 2019, now Pat. No. 10,542,968, which is a
(Continued)

(51) Int. Cl.
*A61B 17/04*     (2006.01)
*A61B 17/062*     (2006.01)
(Continued)

(52) U.S. Cl.
CPC .......... *A61B 17/0401* (2013.01); *A61B 17/04* (2013.01); *A61B 17/0469* (2013.01);
(Continued)

(58) Field of Classification Search
CPC . A61B 17/0057; A61B 17/04; A61B 17/0401; A61B 17/0409; A61B 17/0469;
(Continued)

(56) References Cited

U.S. PATENT DOCUMENTS

| 1,327,577 A | 1/1920 | Turner |
| 1,822,330 A | 9/1931 | Ainslie |

(Continued)

FOREIGN PATENT DOCUMENTS

| CN | 2169381 | 6/1994 |
| CN | 201082170 | 7/2008 |

(Continued)

*Primary Examiner* — Robert A Lynch
(74) *Attorney, Agent, or Firm* — Winthrop & Weinstine, P.A.

(57) ABSTRACT

In accordance with an aspect of the present disclosure, an apparatus for suturing tissue is provided that includes a body having a proximate end and a distal end. A suturing head is coupled to the distal end of the body, including a first set of curved needles, a second set of curved needles, and a plurality of sutures. A first end of a suture is coupled to one of the curved needles of the first set. A second end of the suture is coupled to one of the curved needles of the second set. The curved needles of the first set are oppositely oriented to the curved needles of the second set. The suturing head can be positioned between two substantially parallel sections of tissue. An actuator is coupled to the body to deploy the first and second sets of curved needles.

20 Claims, 42 Drawing Sheets

Related U.S. Application Data continuation of application No. PCT/US2018/068342, filed on Dec. 22, 2017.

(60) Provisional application No. 62/438,579, filed on Dec. 23, 2016.

(51) Int. Cl.
*A61B 17/42* (2006.01)
*A61B 17/06* (2006.01)

(52) U.S. Cl.
CPC ............ *A61B 17/06* (2013.01); *A61B 17/062* (2013.01); *A61B 17/42* (2013.01); *A61B 2017/047* (2013.01); *A61B 2017/0409* (2013.01); *A61B 2017/0417* (2013.01); *A61B 2017/0419* (2013.01); *A61B 2017/0427* (2013.01); *A61B 2017/0461* (2013.01); *A61B 2017/0464* (2013.01); *A61B 2017/0472* (2013.01)

(58) Field of Classification Search
CPC ............ A61B 17/0482; A61B 17/0483; A61B 17/0491; A61B 17/062; A61B 17/0625; A61B 17/42; A61B 2017/0409; A61B 2017/0427; A61B 2017/0446; A61B 2017/0459; A61B 2017/0461; A61B 2017/0464; A61B 2017/047; A61B 2017/0472

See application file for complete search history.

(56) References Cited

U.S. PATENT DOCUMENTS

| | | | |
|---|---|---|---|
| 2,327,353 | A | 8/1943 | Karle |
| 2,601,564 | A | 6/1952 | Smith |
| 3,197,997 | A | 8/1965 | Kurtz |
| 3,311,110 | A | 3/1967 | Singerman et al. |
| 3,344,790 | A | 10/1967 | Dorner |
| 3,762,418 | A | 10/1973 | Wasson |
| 3,834,599 | A | 9/1974 | Herr |
| 3,835,912 | A | 9/1974 | Kristensen et al. |
| 3,910,282 | A | 10/1975 | Messer et al. |
| 3,951,261 | A | 4/1976 | Mandel et al. |
| 3,972,418 | A | 8/1976 | Schuler et al. |
| 4,027,608 | A | 6/1977 | Arbuckle |
| 4,074,732 | A | 2/1978 | Wilkens |
| 4,235,177 | A | 11/1980 | Arbuckle |
| 4,327,655 | A | 5/1982 | Addy et al. |
| 4,331,277 | A | 5/1982 | Green |
| 4,437,465 | A | 3/1984 | Nomoto et al. |
| 4,509,945 | A | 4/1985 | Kramann et al. |
| 4,527,564 | A | 7/1985 | Eguchi et al. |
| 4,557,265 | A | 12/1985 | Andersson |
| 4,621,640 | A | 11/1986 | Mulhollan et al. |
| 4,841,888 | A | 6/1989 | Mills et al. |
| 4,899,746 | A | 2/1990 | Brunk |
| 4,957,502 | A | 9/1990 | Takase |
| 5,080,663 | A | 1/1992 | Mills et al. |
| 5,089,012 | A | 2/1992 | Prou |
| 5,174,300 | A | 12/1992 | Bales |
| 5,201,760 | A | 4/1993 | West |
| 5,210,376 | A | 5/1993 | Caviar |
| 5,269,806 | A | 12/1993 | Sardelis et al. |
| 5,305,281 | A | 4/1994 | Lubeck |
| 5,306,281 | A | 4/1994 | Beurrier |
| 5,308,353 | A | 5/1994 | Beurrier |
| 5,318,566 | A | 6/1994 | Miller |
| 5,318,578 | A | 6/1994 | Hasson |
| 5,330,502 | A | 7/1994 | Hassler |
| 5,344,061 | A | 9/1994 | Crainich |
| 5,358,498 | A | 10/1994 | Shave |
| 5,364,408 | A | 11/1994 | Gordon |
| 5,373,101 | A | 12/1994 | Barabolak |
| 5,376,101 | A | 12/1994 | Green et al. |
| 5,387,221 | A | 2/1995 | Bisgaard |
| 5,403,344 | A | 4/1995 | Allen |
| 5,437,681 | A | 8/1995 | Meade et al. |
| 5,454,819 | A | 10/1995 | Knoepfler |
| 5,462,558 | A | 10/1995 | Kolesa et al. |
| 5,472,081 | A | 12/1995 | Kilgrow et al. |
| 5,474,568 | A | 12/1995 | Scott |
| 5,478,344 | A | 12/1995 | Stone et al. |
| 5,478,345 | A | 12/1995 | Stone et al. |
| 5,480,409 | A | 1/1996 | Riza |
| 5,503,266 | A | 4/1996 | Kalbfeld et al. |
| 5,514,159 | A | 5/1996 | Matula et al. |
| 5,540,705 | A | 7/1996 | Meade et al. |
| 5,571,119 | A | 11/1996 | Atala |
| 5,575,800 | A | 11/1996 | Gordon |
| 5,578,044 | A | 11/1996 | Gordon et al. |
| 5,643,295 | A | 7/1997 | Yoon |
| 5,645,552 | A | 7/1997 | Sherts |
| 5,653,718 | A * | 8/1997 | Yoon ................. A61B 17/34 604/174 |
| 5,665,096 | A | 9/1997 | Yoon |
| 5,665,109 | A | 9/1997 | Yoon |
| 5,669,490 | A | 9/1997 | Colligan et al. |
| 5,675,961 | A | 10/1997 | Cerwin et al. |
| 5,709,693 | A | 1/1998 | Taylor |
| 5,713,910 | A | 2/1998 | Gordon et al. |
| 5,715,942 | A | 2/1998 | Li et al. |
| 5,741,277 | A | 4/1998 | Gordon et al. |
| 5,755,729 | A | 5/1998 | de la Torre et al. |
| 5,759,188 | A | 6/1998 | Yoon |
| 5,766,186 | A | 6/1998 | Faraz et al. |
| 5,814,069 | A | 9/1998 | Schulze et al. |
| 5,814,071 | A | 9/1998 | McDevitt et al. |
| 5,830,234 | A | 11/1998 | Wojciechowicz et al. |
| 5,833,695 | A | 11/1998 | Yoon |
| 5,860,992 | A | 1/1999 | Daniel et al. |
| 5,891,160 | A | 4/1999 | Williamson, IV et al. |
| 5,906,273 | A | 5/1999 | Pohle et al. |
| 5,908,426 | A | 6/1999 | Pierce |
| 5,908,428 | A | 6/1999 | Scirica et al. |
| 5,911,727 | A | 6/1999 | Taylor |
| 5,954,733 | A | 9/1999 | Yoon |
| 5,968,077 | A | 10/1999 | Wojciechowicz et al. |
| 5,993,466 | A | 11/1999 | Yoon |
| 6,016,905 | A | 1/2000 | Gemma et al. |
| 6,036,694 | A | 3/2000 | Goble et al. |
| 6,048,351 | A | 4/2000 | Gordon et al. |
| 6,053,908 | A | 4/2000 | Crainich et al. |
| 6,056,771 | A | 5/2000 | Proto |
| 6,071,289 | A | 6/2000 | Stefanchik et al. |
| 6,096,051 | A | 8/2000 | Kortenbach et al. |
| 6,126,666 | A | 10/2000 | Trapp et al. |
| 6,135,385 | A | 10/2000 | Martinez de Lahidalga |
| 6,136,010 | A | 10/2000 | Modesitt et al. |
| 6,159,224 | A | 12/2000 | Yoon |
| 6,261,307 | B1 | 7/2001 | Yoon et al. |
| 6,270,508 | B1 | 8/2001 | Klieman et al. |
| 6,322,581 | B1 | 11/2001 | Fukuda et al. |
| 6,332,888 | B1 | 12/2001 | Levy et al. |
| 6,346,111 | B1 | 2/2002 | Gordon et al. |
| 6,443,962 | B1 | 9/2002 | Gaber |
| 6,454,777 | B1 | 9/2002 | Green |
| 6,454,778 | B2 | 9/2002 | Kortenbach |
| 6,494,888 | B1 | 12/2002 | Laufer et al. |
| 6,506,196 | B1 | 1/2003 | Laufer |
| 6,558,400 | B2 | 5/2003 | Deem et al. |
| 6,656,194 | B1 | 12/2003 | Gannoe et al. |
| 6,663,639 | B1 | 12/2003 | Laufer et al. |
| 6,719,763 | B2 | 4/2004 | Chung et al. |
| 6,719,764 | B1 | 4/2004 | Gellman et al. |
| 6,746,460 | B2 | 6/2004 | Gannoe et al. |
| 6,755,843 | B2 | 6/2004 | Chung et al. |
| 6,835,200 | B2 | 12/2004 | Laufer et al. |
| 6,877,352 | B1 | 4/2005 | Schlereth |
| 6,908,427 | B2 | 6/2005 | Fleener et al. |
| 6,923,819 | B2 | 8/2005 | Meade et al. |
| 6,955,643 | B2 | 10/2005 | Gellman et al. |
| 7,004,951 | B2 | 2/2006 | Gibbens, III |

(56) References Cited

U.S. PATENT DOCUMENTS

| | | |
|---|---|---|
| 7,033,370 B2 | 4/2006 | Gordon et al. |
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chee Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2007/0239206 A1 | 10/2007 | Shelton, IV et al. |
| 2008/0132919 A1 | 6/2008 | Chui et al. |
| 2008/0140091 A1 | 6/2008 | DeDeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2013/0046319 A1 | 2/2013 | Arnett et al. |
| 2013/0178877 A1* | 7/2013 | Bender ............. A61B 17/0469 606/153 |
| 2014/0163584 A1* | 6/2014 | Rohl ................. A61B 17/0469 606/144 |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 1733685 | 12/2006 |
| EP | 1839591 A1 | 10/2007 |
| EP | 2103262 | 9/2009 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 9/1908 |
| JP | 556270 | 1/1980 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005080761 | 3/2005 |
| JP | 2005253987 | 9/2005 |
| RU | 1827189 C | 7/1993 |
| WO | WO9609796 | 4/1996 |
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | WO02102226 | 12/2002 |
| WO | WO2003028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |

(56) References Cited

FOREIGN PATENT DOCUMENTS

| | | |
|---|---|---|
| WO | WO2007089603 | 8/2007 |
| WO | WO2008147555 | 12/2008 |
| WO | WO2010062380 | 6/2010 |

\* cited by examiner

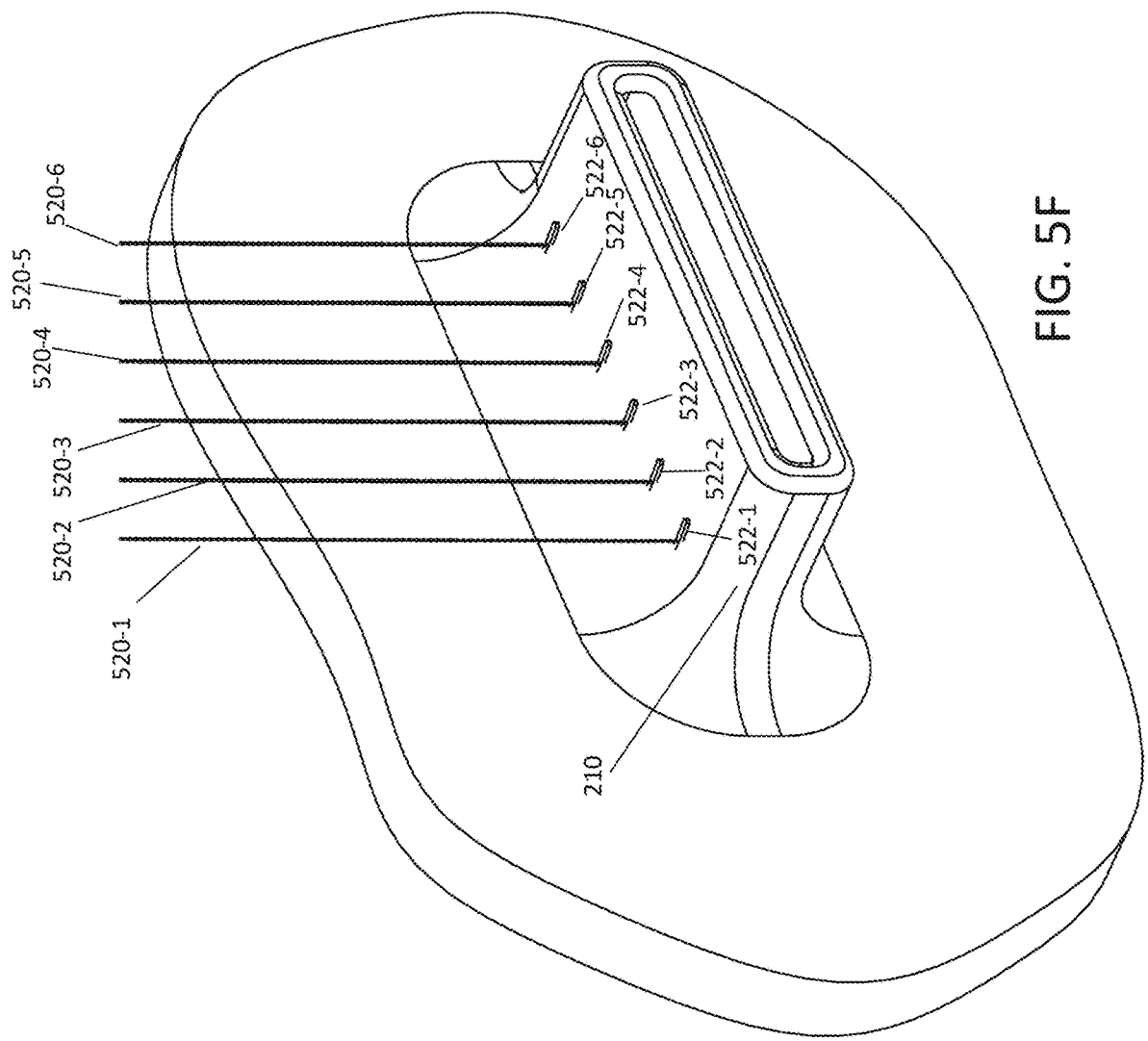

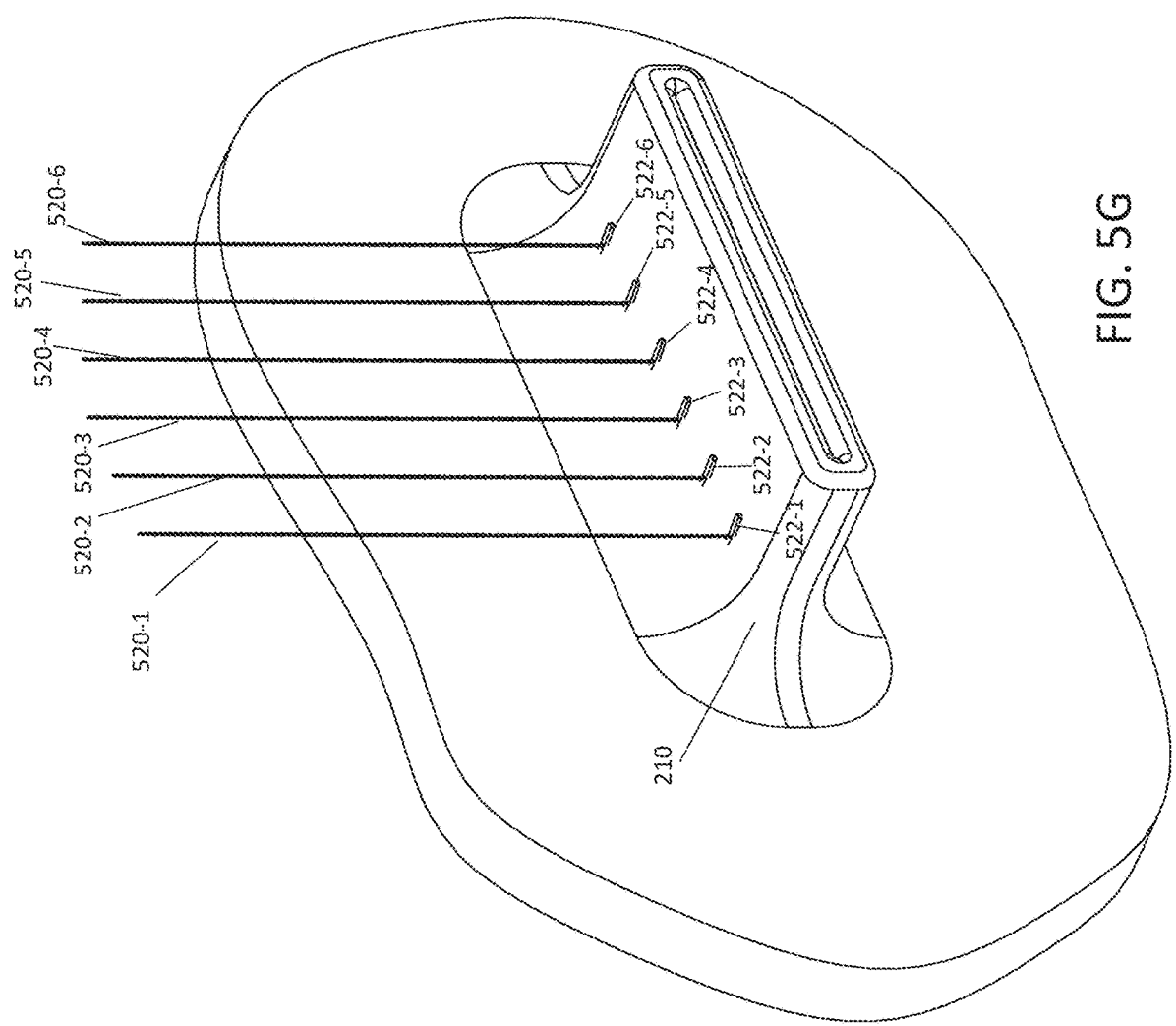

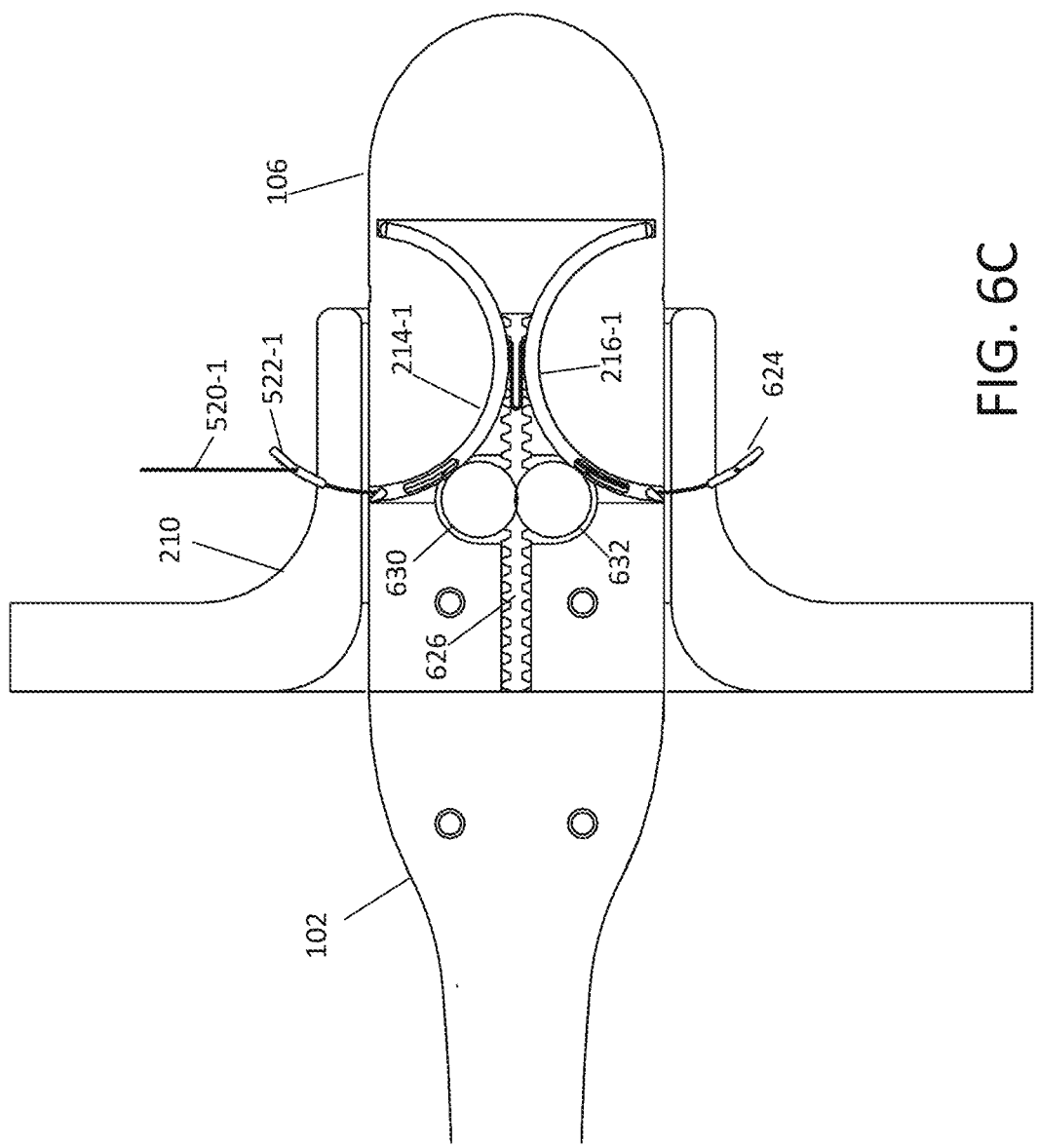

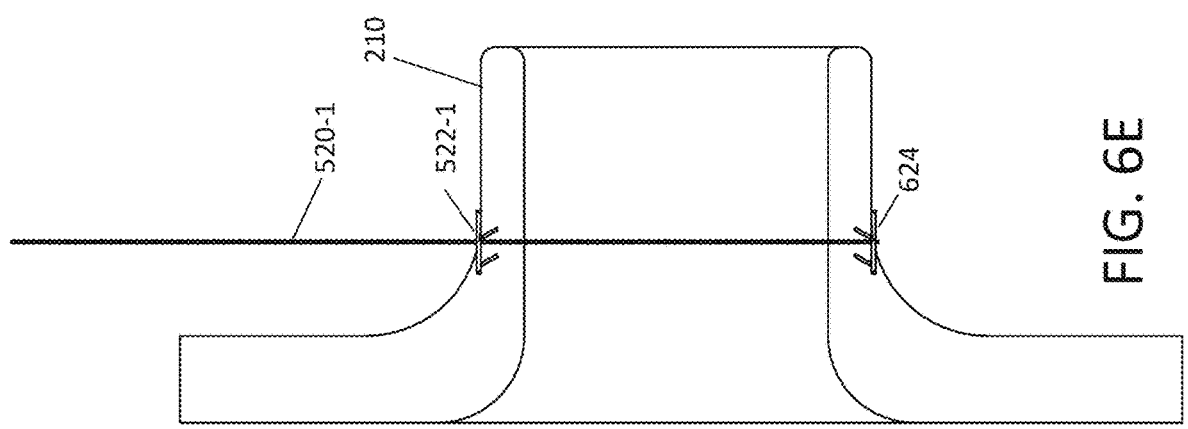

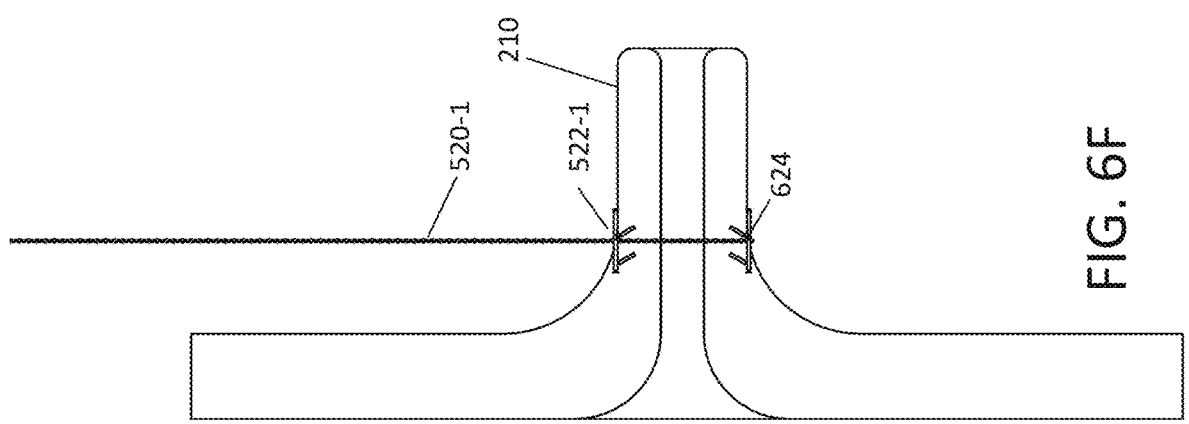

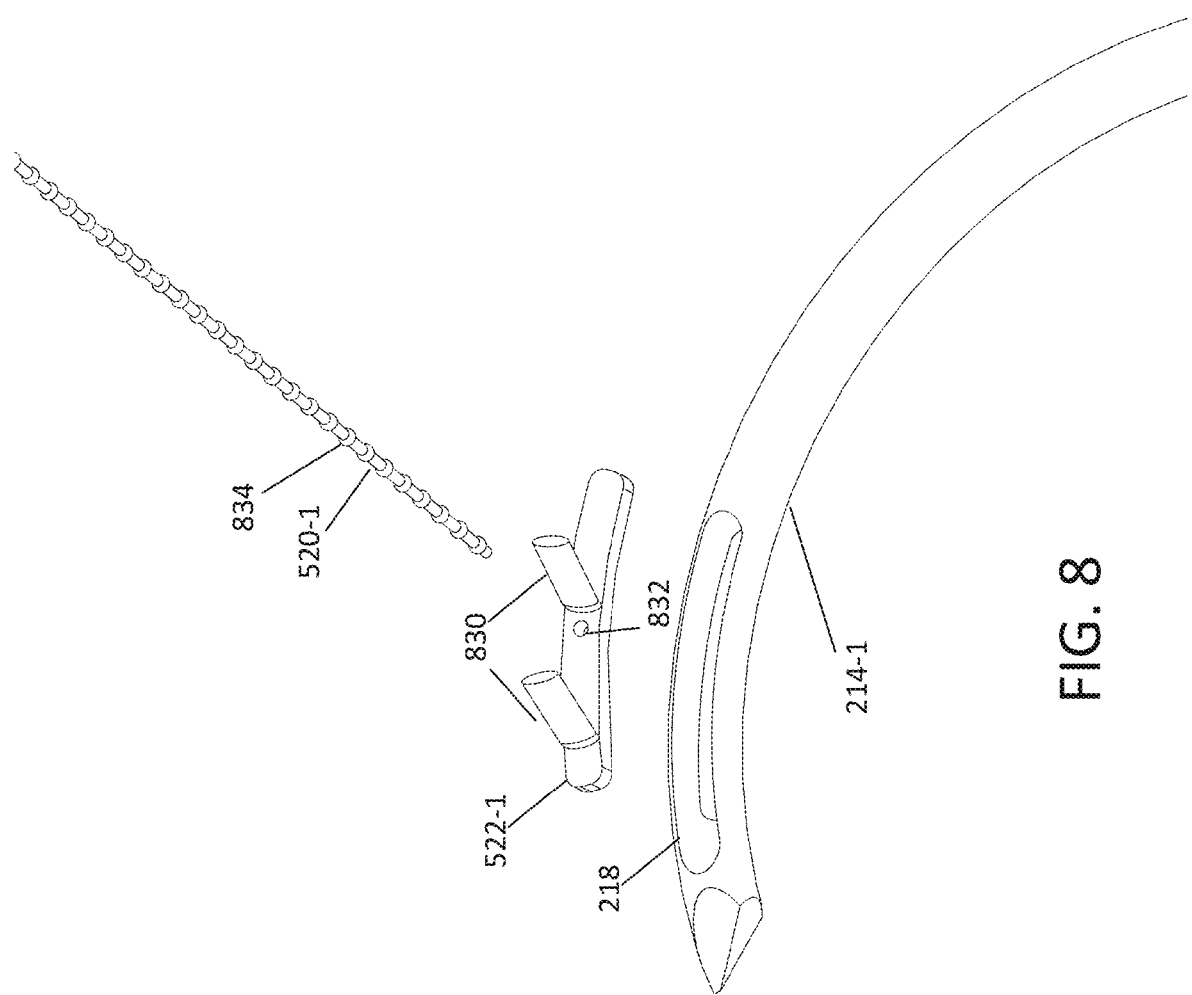

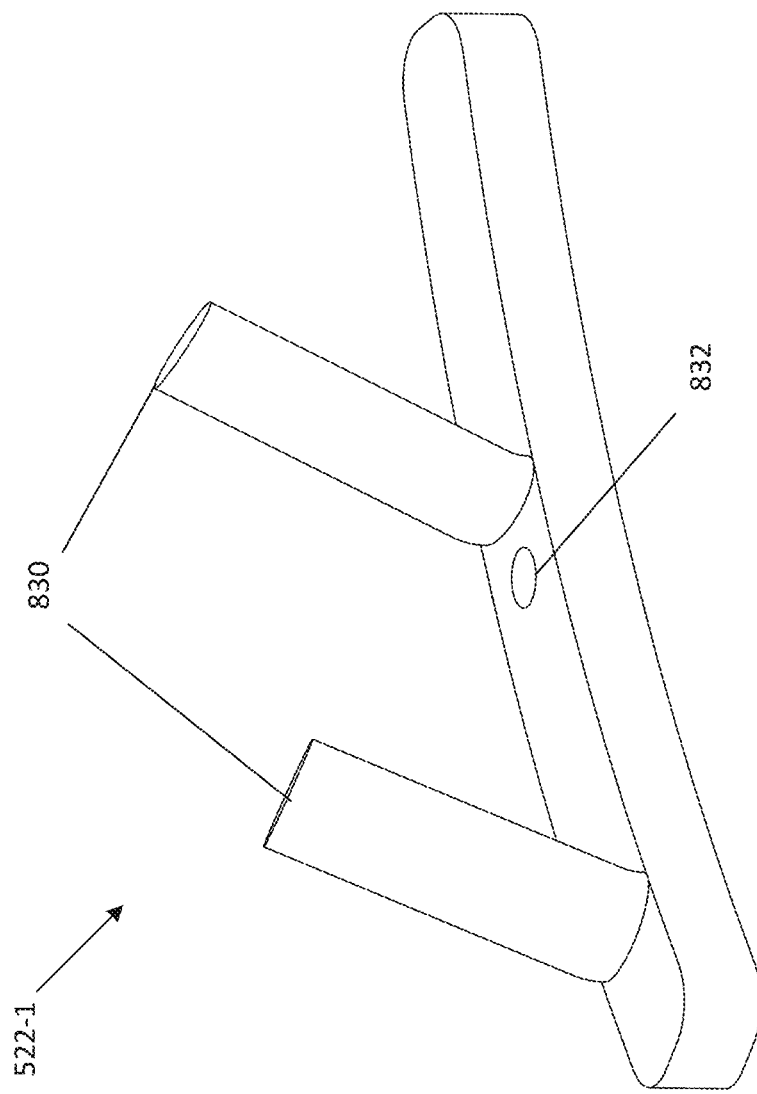

SYSTEMS AND METHODS FOR SUTURING TISSUE

CROSS-REFERENCE TO RELATED APPLICATIONS

The present patent application is a continuation of and claims the benefit of priority to U.S. patent application Ser. No. 16/368,495, filed Mar. 28, 2019, and issued Jan. 28, 2020 as U.S. Pat. No. 10,542,968, which in turn is a continuation of and claims the benefit of priority to International Application No. PCT/US2017/068342 filed Dec. 22, 2017, which in turn claims the benefit of priority to U.S. Provisional Patent Application Ser. No. 62/438,579, filed Dec. 23, 2016. Each of the aforementioned patent applications is incorporated herein by reference in its entirety for any purpose whatsoever.

TECHNICAL FIELD

Various aspects of the present disclosure relate generally to surgical devices and methods. More specifically, the present disclosure relates to tissue suturing devices and related methods for minimally invasive surgery.

BACKGROUND

Laparoscopic suturing is challenging and may take years for a surgeon to master. For example, suturing the vaginal cuff during a total laparoscopic hysterectomy (TLH) is often the rate limiting step due to the dexterity and coordination required for suturing. In the United States alone, there are approximately 300,000 laparoscopic or robotic hysterectomies performed annually. In such procedures, the cervix is severed from the vagina and removed with the uterus, leaving behind the opening in the vaginal wall that must be closed. However, the geometry of this opening can make it difficult to suture effectively. Consequently, vaginal cuff dehiscence is a potentially catastrophic event where the vaginal cuff opens such that the bowel may herniate through the vagina. Bowel herniation through the vagina may require immediate surgery. The incidence of vaginal cuff dehiscence after a TLH has been found to be approximately 0.5-4%. A modifiable risk factor for vaginal cuff dehiscence is surgical technique, which has significant inter-operator variability. The present disclosure provides solutions for these problems.

SUMMARY

The present disclosure is directed to devices and related methods for consistently and quickly suturing tissue, such as the vaginal cuff that results from separation of the cervix from the vagina. Disclosed devices are configured and adapted for introduction into the patient via the vagina, wherein a distal suturing head portion of the disclosed devices are sized and shaped to be introduced into the vaginal cuff by way of the vagina to effectuate fast, safe and effective suturing of the vaginal cuff.

Aspects of the present disclosure relate to, among other things, tissue extraction devices and related methods. Each of the aspects disclosed herein may include one or more of the features described in connection with any of the other disclosed aspects.

It may be understood that both the foregoing general description and the following detailed description are exemplary and explanatory only and are not restrictive of the features claimed.

As used herein, the terms "comprises," "comprising," or any other variation thereof, are intended to cover a non-exclusive inclusion such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

An illustrative apparatus for suturing tissue comprises a body having a proximate end and a distal end, a suturing head coupled to the distal end of the body, and an actuator coupled to the body. The suturing head including a first set of curved needles disposed therein, a second set of curved needles disposed therein, and a plurality of sutures disposed therein. A first end of a respective one of the plurality of sutures is coupled to a respective one of the curved needles of the first set. A second end of the respective one of the plurality of sutures is coupled to a respective one of the curved needles of the second set. The curved needles of the first set are oppositely oriented to the curved needles of the second set. The suturing head is configured and arranged to be positioned between two substantially parallel sections of tissue (e.g., the vaginal cuff). The actuator is configured and arranged to deploy the first and second sets of curved needles through the tissue to suture the two sections of tissue together in a single operation.

The apparatus further comprises a first anchor slidably coupled to a respective one of the sutures and a respective one of the curved needles of the first set and a second anchor fixedly coupled proximate an end of the suture and a respective one of the curved needles of the second set. A portion of the suture includes an end of the suture is free floating on one side of the first anchor.

The first and second anchors can be configured and arranged to pass through from a first surface of one of the sections of tissue to a second surface of one of the sections of tissue while coupled to the curved needle and separate from the curved needle and remain on the second surface subsequent to actuation of the suturing head.

Each of the curved needles can include at least one aperture on a surface of the curved needle. The first anchor can be initially positioned within the aperture of the curved needles of the first set. The second anchor can be initially positioned within the aperture of the curved needles of the second set. Each of the curved needles can includes another aperture on the surface of the curved needle. The suture can pass through the aperture and the other aperture.

Each of the curved needles can include a first, relatively proximal region having a first diameter and a second, relatively distal region having a second diameter. The distal region includes a distal tip of the curved needle. The second diameter is smaller than the first diameter. The first and second anchors are coupled to the curved needles in the distal region.

The first anchor can be configured and arranged to traverse the suture towards the second anchor to suture the two substantially parallel sections of tissue together. Each of the sutures can include a plurality of bumps along the suture that inhibit the traversal of the first anchor along the suture.

The actuator can includes a trigger coupled to the body configured and arranged to deploy the first and second sets of curved needles. The trigger is coupled to a proximate end of an elongated member coupled to the suturing head. The suturing head and the elongated member cooperate to form a plurality of racks and pinions formed by racks of a distal end of the elongated member and pinions of the suturing head. The curved needles are coupled to the pinions such that rotation of a respective one of the pinions in a first direction causes rotation of the curved needles away from the suturing head in a second direction opposite to the first direction.

The actuator can include a knob coupled to the body configured and arranged to deploy the first and second sets of curved needles. The curved needles of the first set are coupled to a first axle and the curved needles of the second set are coupled to a second axle (2232). The knob is coupled to a belt coupled to a gear of the first axle and a gear of the second axle.

The curved needles of the first and second sets can be arcuate needles.

The two substantially parallel sections of tissue can be an anterior section and a posterior section of a separated vaginal cuff. The suturing head can fit within the separated vaginal cuff.

The suturing head can include at least one alignment marking to position the suturing head between the two substantially parallel sections of tissue.

The suturing head can be removably coupled to the distal end of the body.

A method of suturing tissue comprises positioning a first set of curved needles and a second set of curved needles between two substantially parallel sections of tissue. The curved needles of the first set are oppositely oriented to the curved needles of the second set. The method can include simultaneously (or serially, if desired) deploying the sets of curved needles such that the curved needles of the first set pass through a first section of tissue and the curved needles of the second set pass through a second section of tissue and positioning a pair of anchors, coupled to a suture, proximate a surface of the first section of tissue and a surface of the second section tissue. A first anchor of the pair is coupled to one of the curved needles of the first set and a second anchor of the pair is coupled to one of the curved needles of the second set. The method includes removing the sets of curved needles from between the sections of tissue. The method includes ratcheting a first anchor of the pair along the suture and towards a second anchor of the pair to suture the first section of tissue to the second section of tissue.

Deploying the sets of curved needles can include serially or simultaneously rotating the curved needles of the first set in a first direction about a center point of the curved needles of the first set and rotating the curved needles of the second set in a second direction, opposite to the first direction, about the center point of the curved needles of the second set. Removing the sets of curved needles can include serially or simultaneously rotating the curved needles of the first set in the second direction about the center point of the curved needles of the first set and rotating the curved needles of the second set in the first direction about the center point of the curved needles of the second set.

Deploying the sets of curved needles can include serially, or simultaneously, rotating the curved needles of the first set in a first direction about a first axle coupled to the curved needles of the first set and rotating the curved needles of the second set in a second direction, opposite to the first direction, about a second axle coupled to the curved needles of the second set. Removing the sets of curved needles can include serially, or simultaneously, rotating the curved needles of the first set in the second direction about the first axle and rotating the curved needles of the second set in the first direction about the second axle.

Positioning the pair of anchors can include separating the first anchor from the curved needle of the first set and the second anchor from the curved needle of the second set.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 5A-5G illustrate suturing tissue using the suturing device of FIG. 1A.

FIGS. 6A-6G illustrate a sectional view of suturing tissue using the suturing device of FIG. 1A.

FIG. 8 is an exploded view of a curved needle, anchor, and suture, in accordance with aspects of the present disclosure.

FIG. 9 is a view of an anchor, in accordance with aspects of the present disclosure.

DETAILED DESCRIPTION

The present disclosure is drawn to laparoscopic tissue devices and related methods. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject. The term "approximately," when used to describe a numerical value, may be anywhere in a range of ±5% from the numerical value.

Figure 1A:
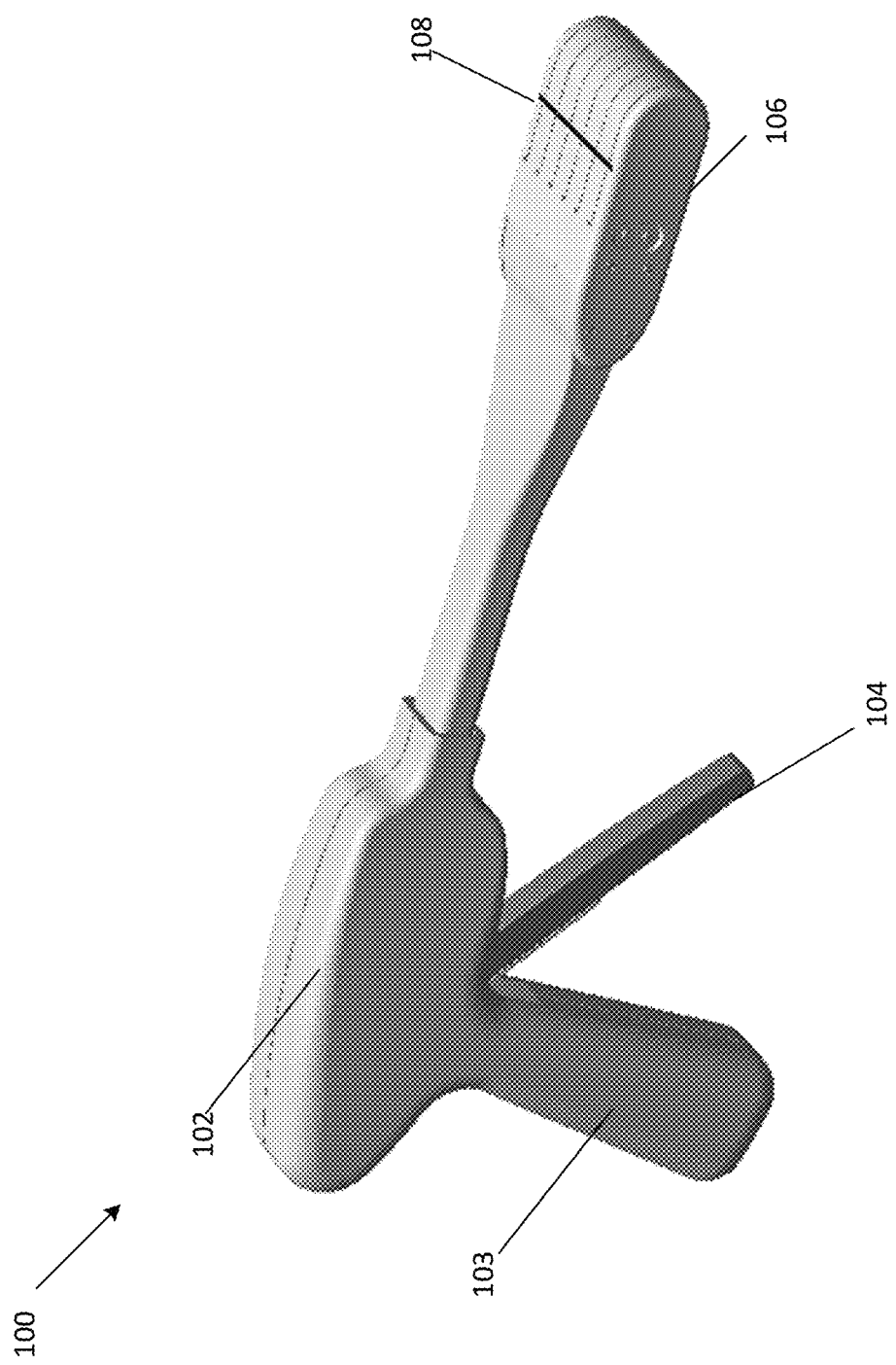
FIG. 1A is a view of a tissue suturing device, in accordance with aspects of the present disclosure.
Figure 1C:
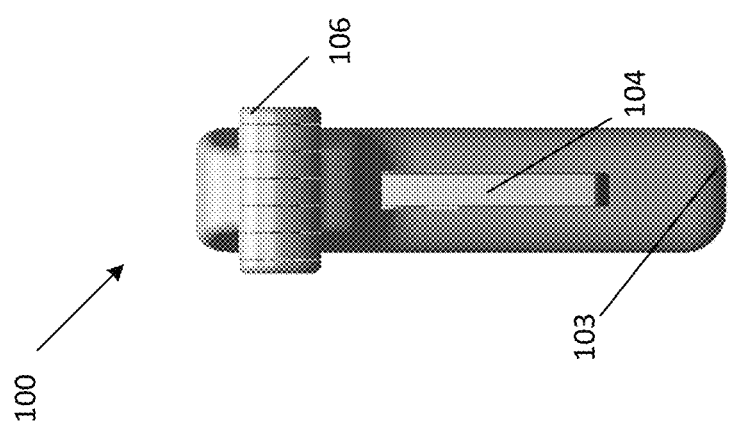
FIG. 1C is an end view of the tissue suturing device of FIG. 1A.
Figure 1B:
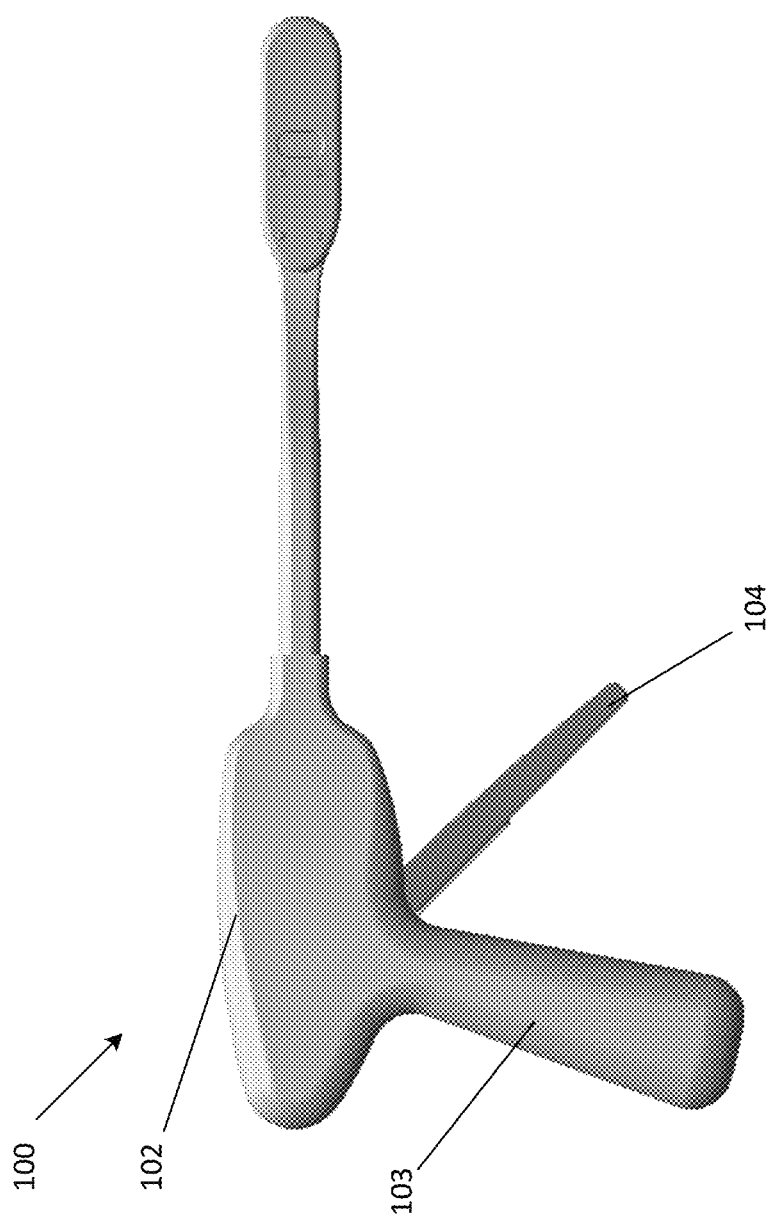
FIG. 1B is a side view of the tissue suturing device of FIG. 1A.

FIG. 1A is a view of a tissue suturing device 100, in accordance with aspects of the present disclosure. The tissue suturing device 100 includes a body 102 having a distal end and a proximal end. A suturing head 106 is coupled to the distal end of the body 102. The suturing head 106 includes at least one alignment marking 108 to aide in aligning the suturing head 106 with the tissue to be sutured. Examples of the alignment marking 108 include, but are not limited to, a radiopaque marking, a fluoroscopic marking, and an indentation. A handle 103 is coupled to the proximal end of the body 102. A trigger 104 is coupled to the handle 103 and/or the body 102. The trigger 104 deploys curved needles from the suturing head 106, which is discussed further in association with FIGS. 16-18 below. FIG. 1B is a side view of the tissue suturing device 100 of FIG. 1A. FIG. 1C is an end view of the tissue suturing device 100 of FIG. 1A.

Figure 2:
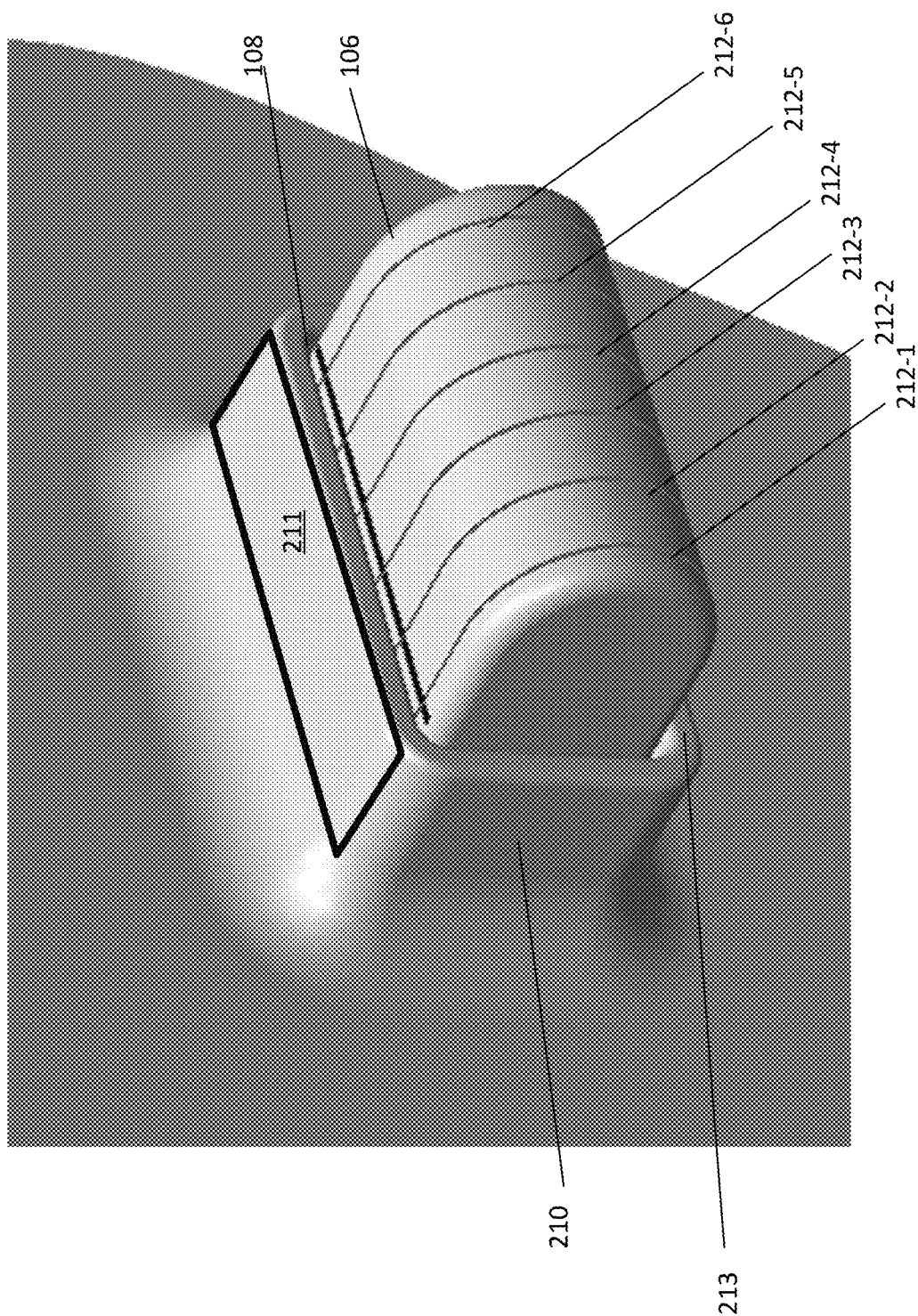
FIG. 2 is a view of a suturing head of the tissue suturing device of FIG. 1A aligned in a separated vaginal cuff arising, for example from separation of the cervix from the vagina as a result of performing a hysterectomy, wherein the suturing device is introduced into the region of the cuff by inserting it into the patient by way of the vagina.

FIG. 2 is a view of the suturing head 106 of the tissue suturing device 100 of FIG. 1A aligned in a separated vaginal cuff 210. The suturing head 106 can be inserted into the patient by way of the vagina. The suturing head 106 can fit in the separated vaginal cuff 210. The vaginal cuff is typically created during a hysterectomy by separating the uterus and cervix from the vagina. For example, the suturing head 106 can be 40 mm wide and 20 mm thick. The suturing head 106 can be inserted in the vaginal cuff 210 with the assistance of laparoscopic video to help visualize when the suturing device has been placed through the cuff to a desired extent in the desired orientation. The alignment marking 108 is used to align the suturing head 106 in the vaginal cuff 210. For example, the alignment marking can position curved needles of the suturing head 106 ten millimeters (mm) from an edge of the vaginal cuff 210. Although the present disclosure uses a separated vaginal cuff as an example, embodiment in accordance with the present disclosure can be used to suture any two substantially parallel sections of tissue. For example, the vaginal cuff 210 includes a first section of tissue 211 (e.g., an anterior section) and a second section of tissue 213 (e.g., a posterior section).

The suturing head 106 includes a plurality of slits 212-1, 212-2, 212-3, 212-4, 212-5, and 212-6 (collectively referred to as the slits 212). A suture is removed from the suturing head 106 through each of the slits 212 subsequent to deployment and retraction of curved needles.

Figure 3:
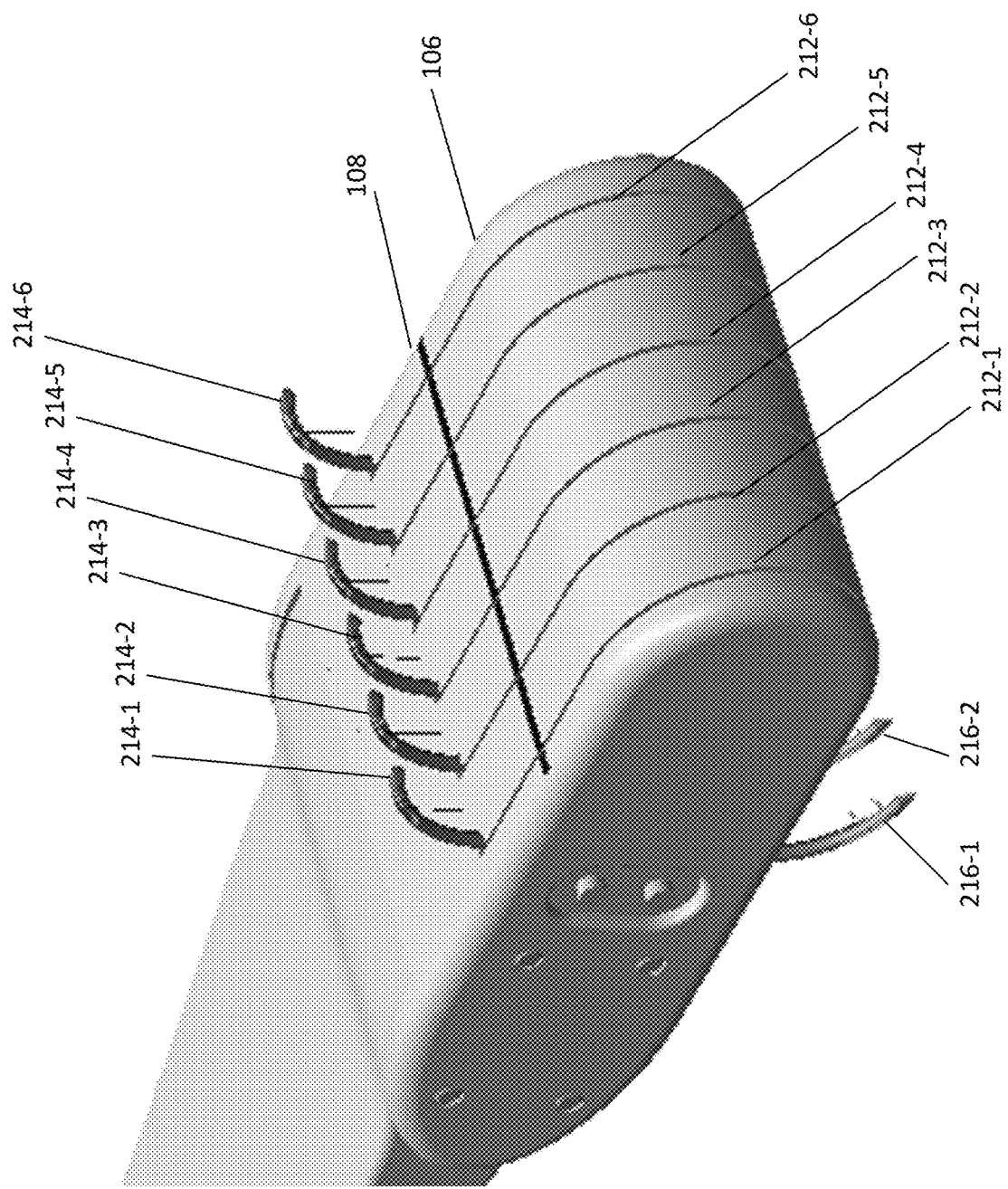
FIG. 3 is a view of a suturing head of the tissue suturing device of FIG. 1A with sets of curved needles deployed.

FIG. 3 is a view of a suturing head of the tissue suturing device 100 of FIG. 1A with sets of curved needles deployed. A first set of curved needles includes curved needles 214-1, 214-2, 214-3, 214-4, 214-5, and 214-6 (collectively referred to as the first set 214). A second set of curved needles 216-1, 216-2, 216-3, 216-4, 216-5, and 216-6 (collectively referred to as the second set 216). In FIG. 3, only curved needles 216-1 and 216-2 are visible; however, the second set 216 is deployed simultaneously with the first set 214, in the illustrated embodiment. Deployment of the first set 214 and the second set 216 is discussed further in association with FIGS. 5A-7E below. It will be appreciated, however, that the device can alternatively be configured to deploy the first and second sets of curved needles at different times. It will be further appreciated that the device can still alternatively be configured to deploy needles in each group serially so as to reduce stress on drive components.

Figures 4A, 4B:
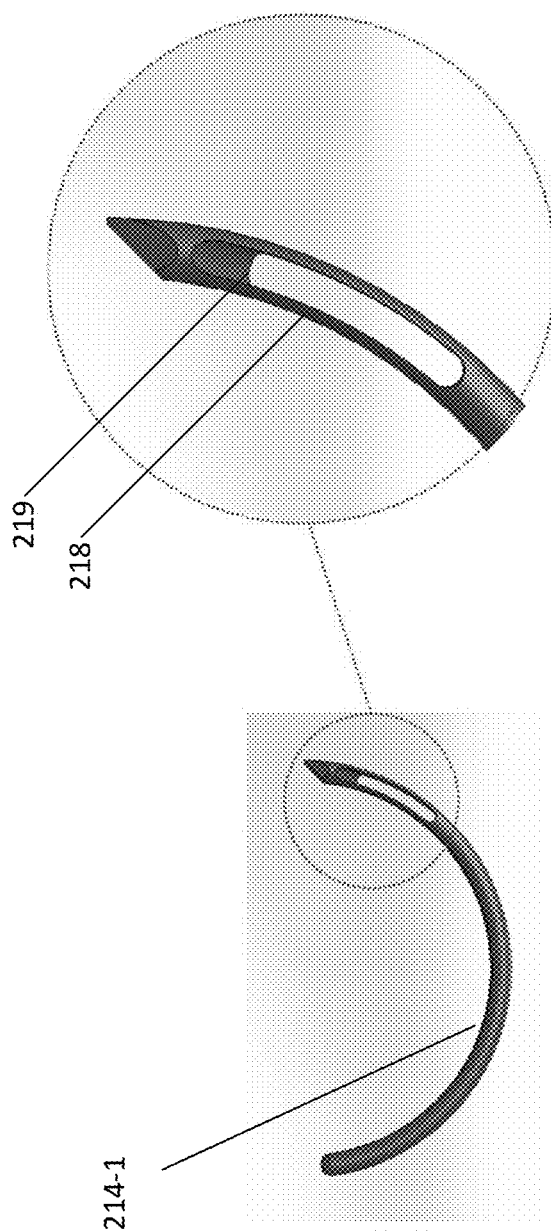
FIG. 4A is a side view of a curved needle, in accordance with aspects of the present disclosure.
FIG. 4B is an enlarged view of a tip of the curved needle of FIG. 4A.

FIG. 4A is a side view of a curved needle 214-1, in accordance with aspects of the present disclosure. In at least one embodiment, the diameter of the needle can be one mm. FIG. 4B is an enlarged view of a tip of the curved needle 214-1. The curved needle 214-1 includes at least one aperture on a surface of the curved needle 214-1. The curved needle 214-1 includes a first aperture 218 on the surface of curved needle 214-1. In at least one embodiment, the length of the first aperture 218 can be 4 mm. The curved needle 214-1 includes a second aperture 219 on the surface of the curved needle 214-1 and opposite to the first aperture. The suture can pass through the curved needle 214-1 transversely through the first aperture 218 and the second aperture 219. In at least one embodiment, the first aperture 218 is longer along an axis of the curved needle 214-1 than the second aperture 219. Although FIGS. 4A-4B shows the curved needle 214-1, the curved needle 214-1 is analogous to the curved needles 214-2-214-6.

In at least one embodiment, the second set 216 includes curved needles that are mirror images of the curved needle 214-1. That is, the positioning of the first aperture 218 and the second aperture 219 are switched. In at least one embodiment, the curved needles of the first set 214 and the second set 216 are arcuate needles. For example, each of the curved needles can be a quarter arc. The radius of the arc can be nine mm.

Figure 5A:
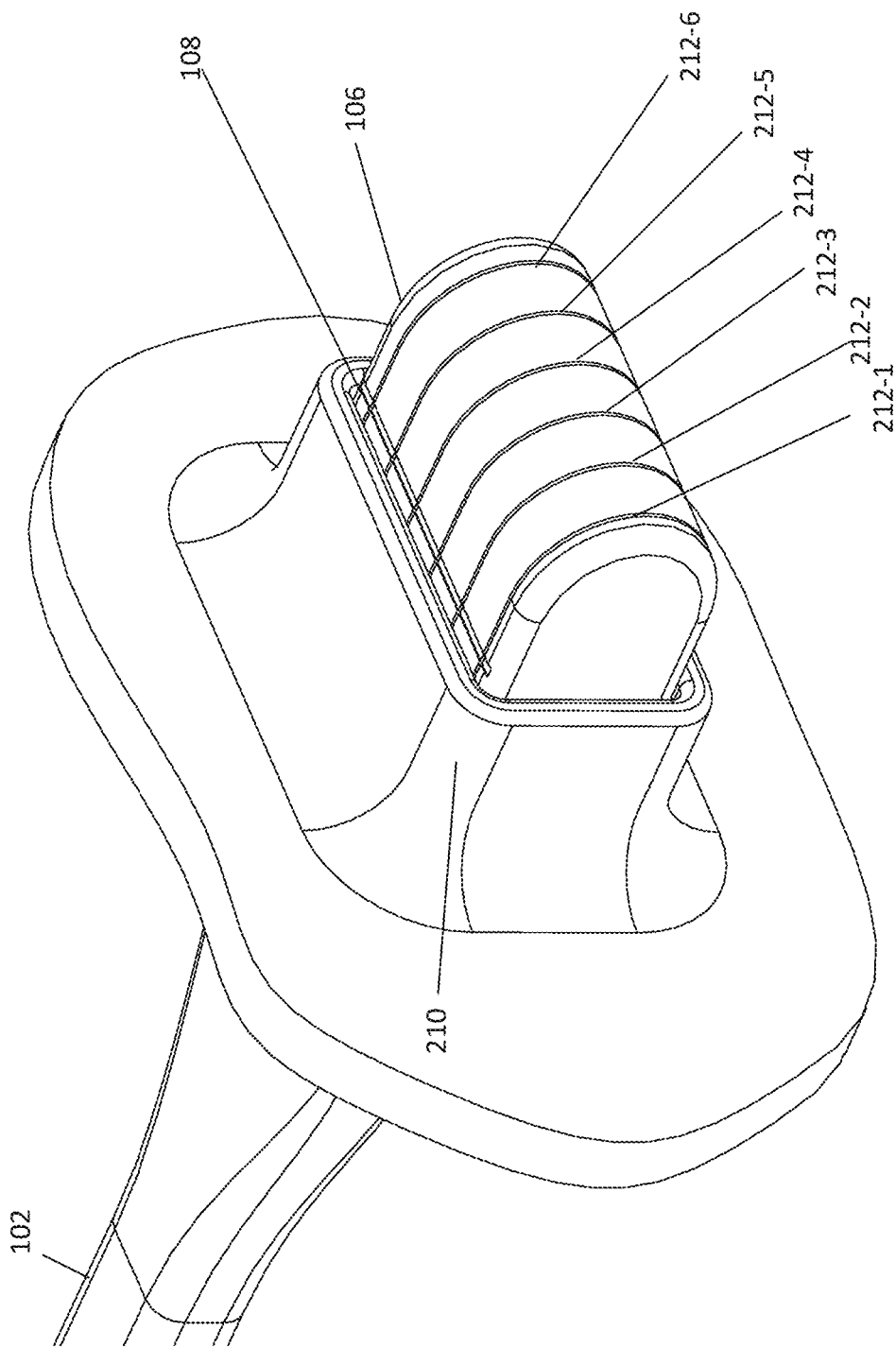
Figure 5B:
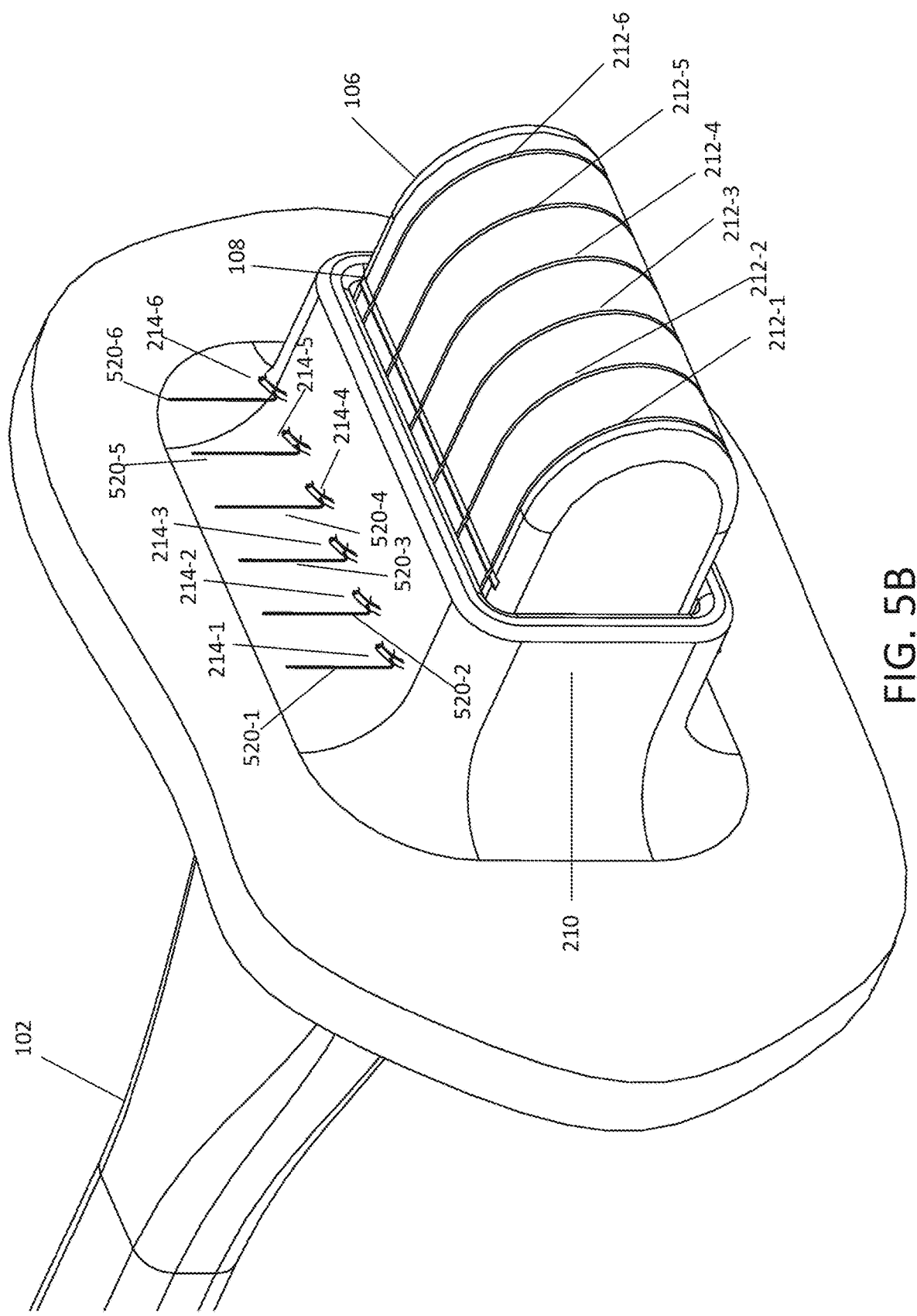

FIGS. 5A-5G illustrate suturing tissue using the suturing device 100 of FIG. 1A. FIG. 5A illustrates the suturing head 106 positioned and aligned in the separated vaginal cuff 210. FIG. 5B illustrates partial deployment of the first set of curved needles 214 and the second set of curved needles 216 (not visible in FIG. 5B). As the first set 214 and the second set 216 are deployed, the curved needles of the first set 214 and the second set 216 pass though the tissue of the vaginal cuff 210. An anchor is coupled to each of the curved needles of the first set 214 and the second set 216, which also passes through the anterior and posterior sections of the vaginal cuff 210. The anchors are coupled to a plurality of sutures 520-1, 520-2, 520-3, 520-4, 520-5, and 520-6 (collectively referred to as the sutures 520). The suturing head 106 can be removably coupled to the body 102 and pre-loaded with the sutures 520. A first anchor is positioned in an aperture of the curved needles of the first set 214. As shown in FIG. 5B, the first anchor is coupled to each of the sutures 520 so that a first end of the sutures 520 is free floating on one side of the first anchor. A second anchor is coupled to a second end of each of the sutures 520. The second end of the sutures 520 are fixedly coupled to the second anchors.

Figure 5C:
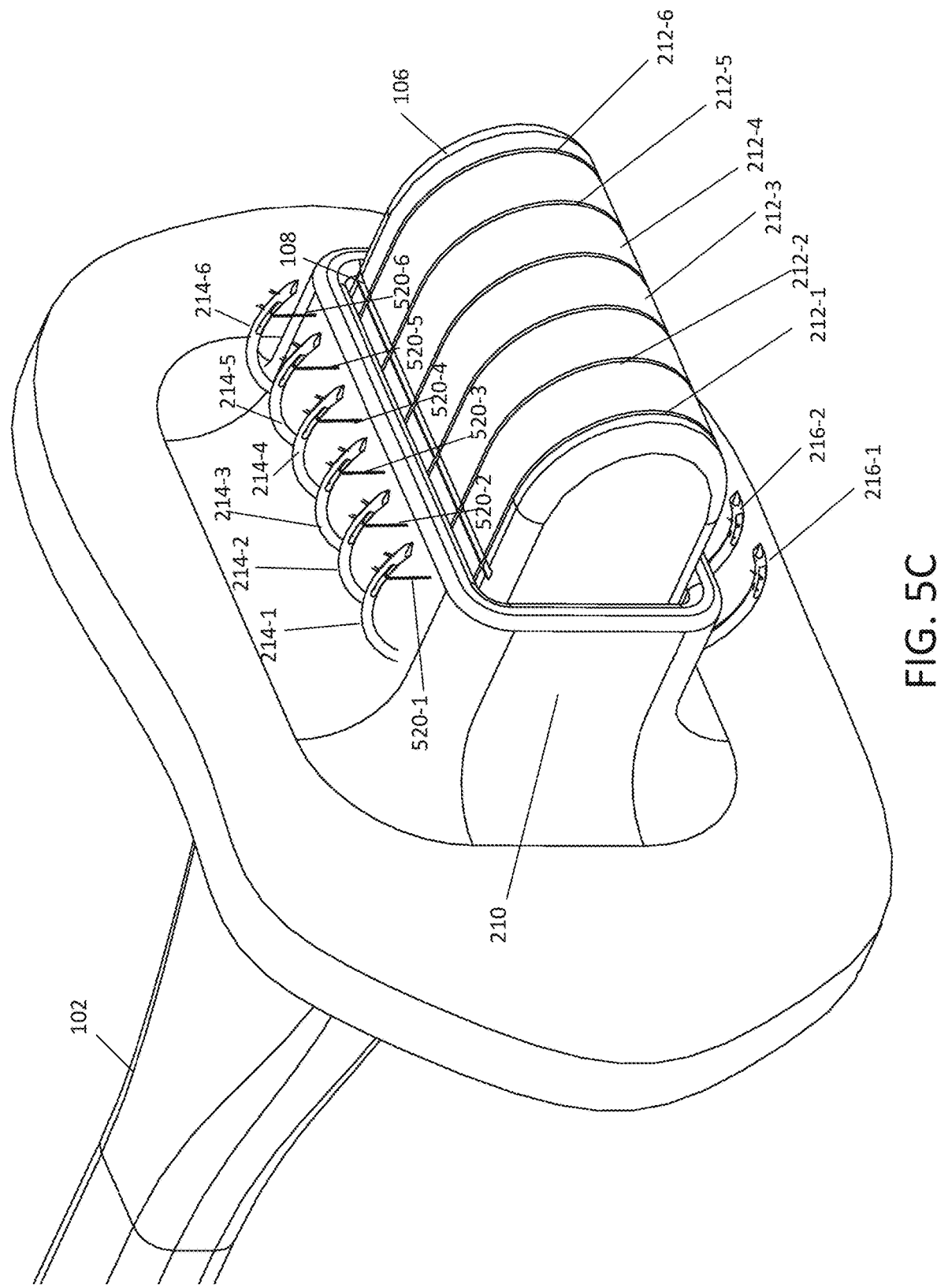

FIG. 5C illustrates full deployment of the first set of curved needles 214 and the second set of curved needles 216 (not visible in FIG. 5B). The anchors are still coupled to the needles of the first set 214 and the second set 216. After the first set 214 and the second set 216 have been deployed, partially or fully, the curved needles retract back into the suturing head 106. The curved needles of the first set 214 and the second set 216 follow the same path for deployment as retraction, but in opposite directions.

Figure 5D:
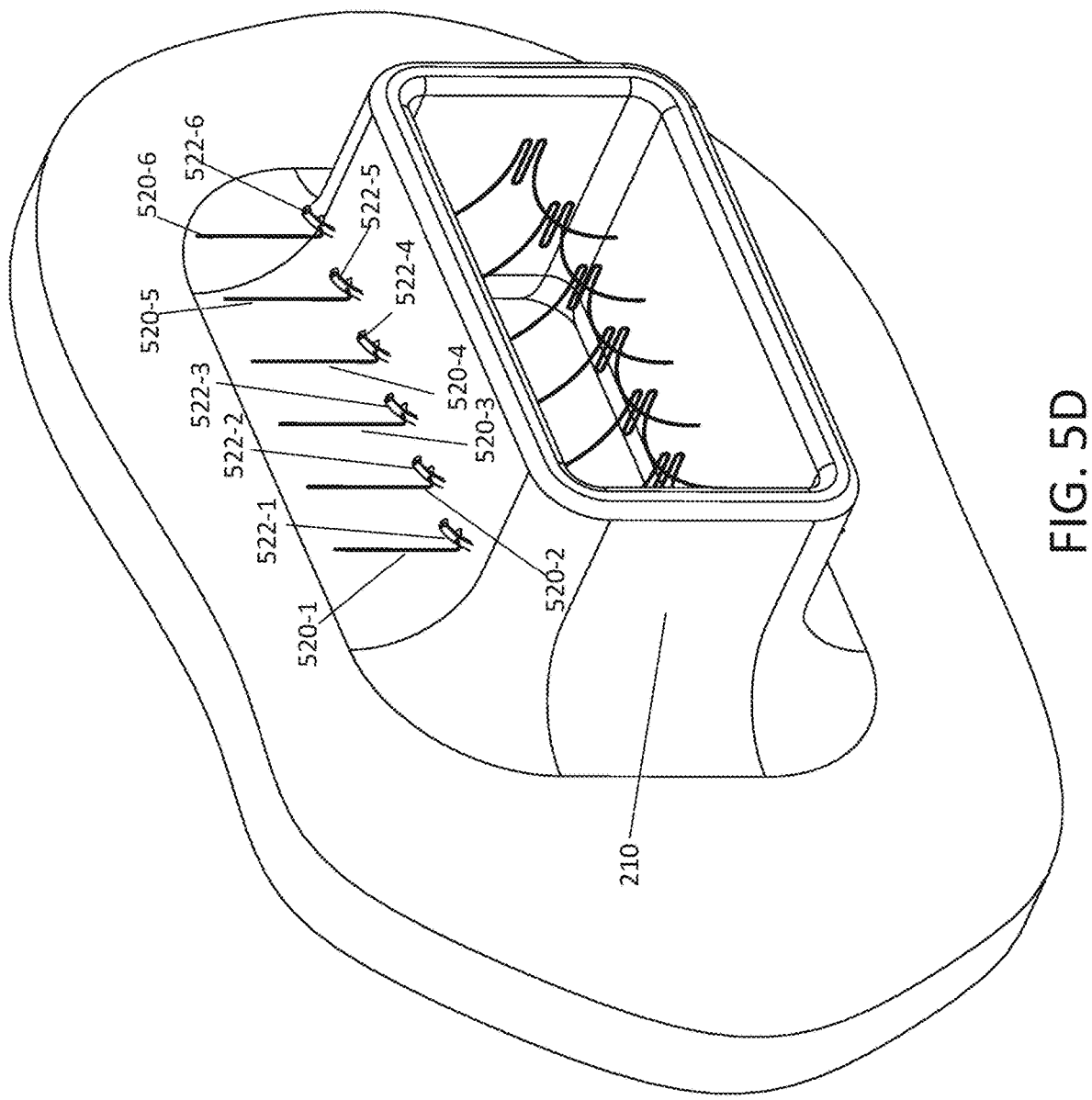

FIG. 5D illustrates anchors positioned on an anterior surface of the separated vaginal cuff 210 after removal of the suturing head 106 from the vaginal cuff 210. The first set 214 and the second set 216 of curved needles have retracted back into the suturing head 106 and the suturing head 106 has been removed from the vaginal cuff 210. The sutures 520 are removed from the suturing head 106 through the slits 216 (illustrated in FIG. 5C) as the suturing head 106 is removed from the vaginal cuff 210. As shown in FIG. 5D, a portion of the sutures 520 can be bunched and/or wound between the anchors and within the separated vaginal cuff 210. The first anchors 522-1, 522-2, 522-3, 522-4, 522-5, and 522-6 (collectively referred to as the first anchors 522) are positioned against the anterior section of tissue of the vaginal cuff 210. Second anchors (not visible in FIG. 5D) are positioned against the posterior section of tissue of the vaginal cuff 210.

Figure 5E:
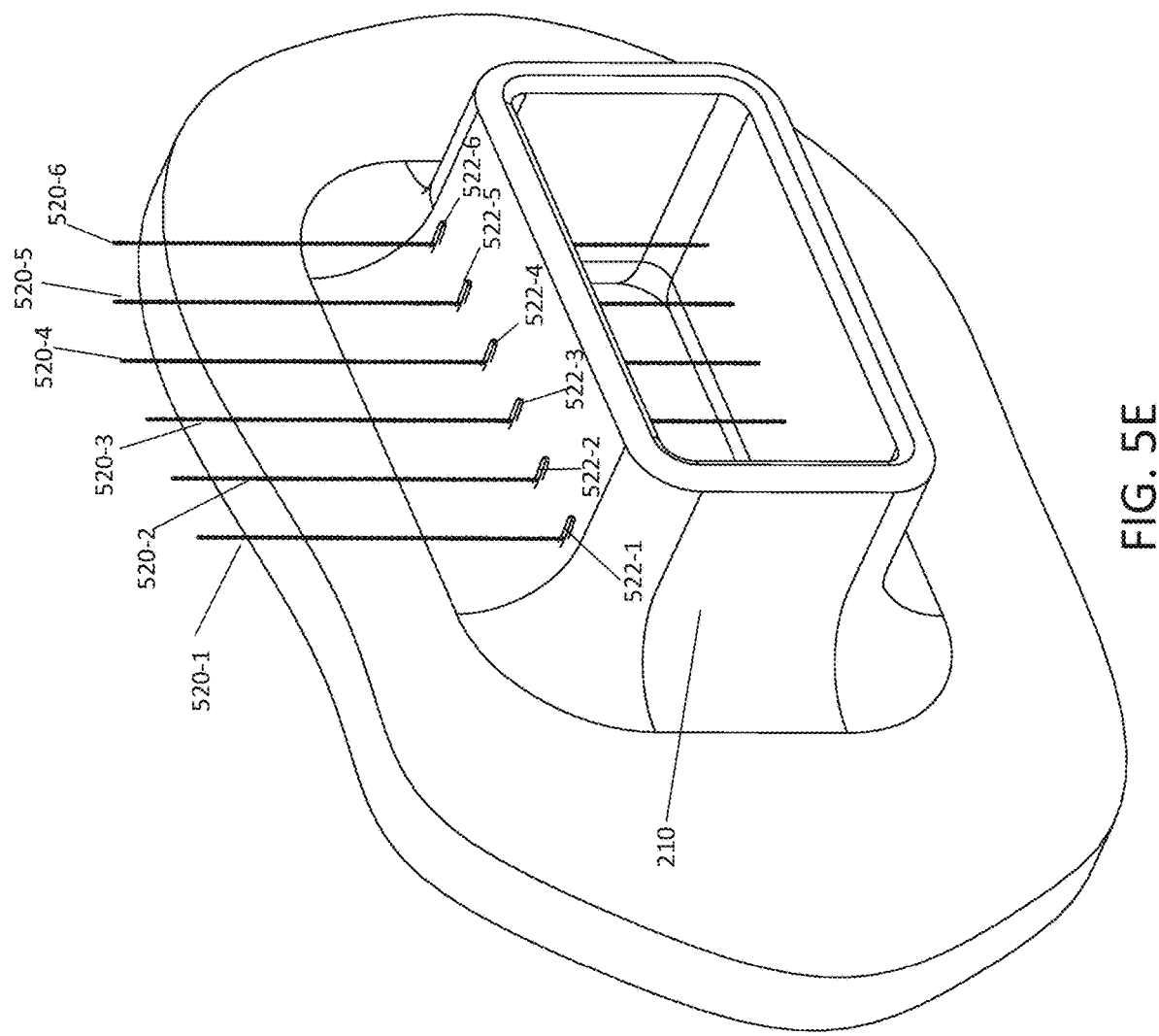

FIG. 5E illustrates the sutures 520 in a tensioned state. Recall that the second end of the sutures 520 are fixedly coupled to the second anchors. As tension is applied to the free floating portion of the sutures 520, the bunched and/or wound portion of the sutures 520 straighten as the sutures 520 are pulled through the first anchors 522. The first anchors 522 traverse the sutures 520 towards the second anchors and the second anchors are pulled towards the first anchors 522.

FIG. 5F illustrates the vaginal cuff 210 in a partially sutured and closed state. As more tension is applied to the sutures 520, the sutures 520 pass through the first anchors 522. Because the second anchors are fixedly coupled to the second end of the sutures 520, the first anchors 522 traverse the sutures 520 towards the second anchors. As a result, the first anchors 522 and/or the second anchors apply a force to the first and second sections of tissue, respectively, to suture and close the separated vaginal cuff 210.

FIG. 5G illustrates the vaginal cuff 210 in a fully sutured and closed state. Tension is applied, for example, by cinching, to the sutures 520 until at least a portion of the anterior and posterior sections of tissues of the vaginal cuff 210 are in contact with each other. At this point, the free floating portion of the sutures 520 on the side of the first anchors 522 can be trimmed and/or tied down to secure the position of the first anchors 522.

Figure 6A:
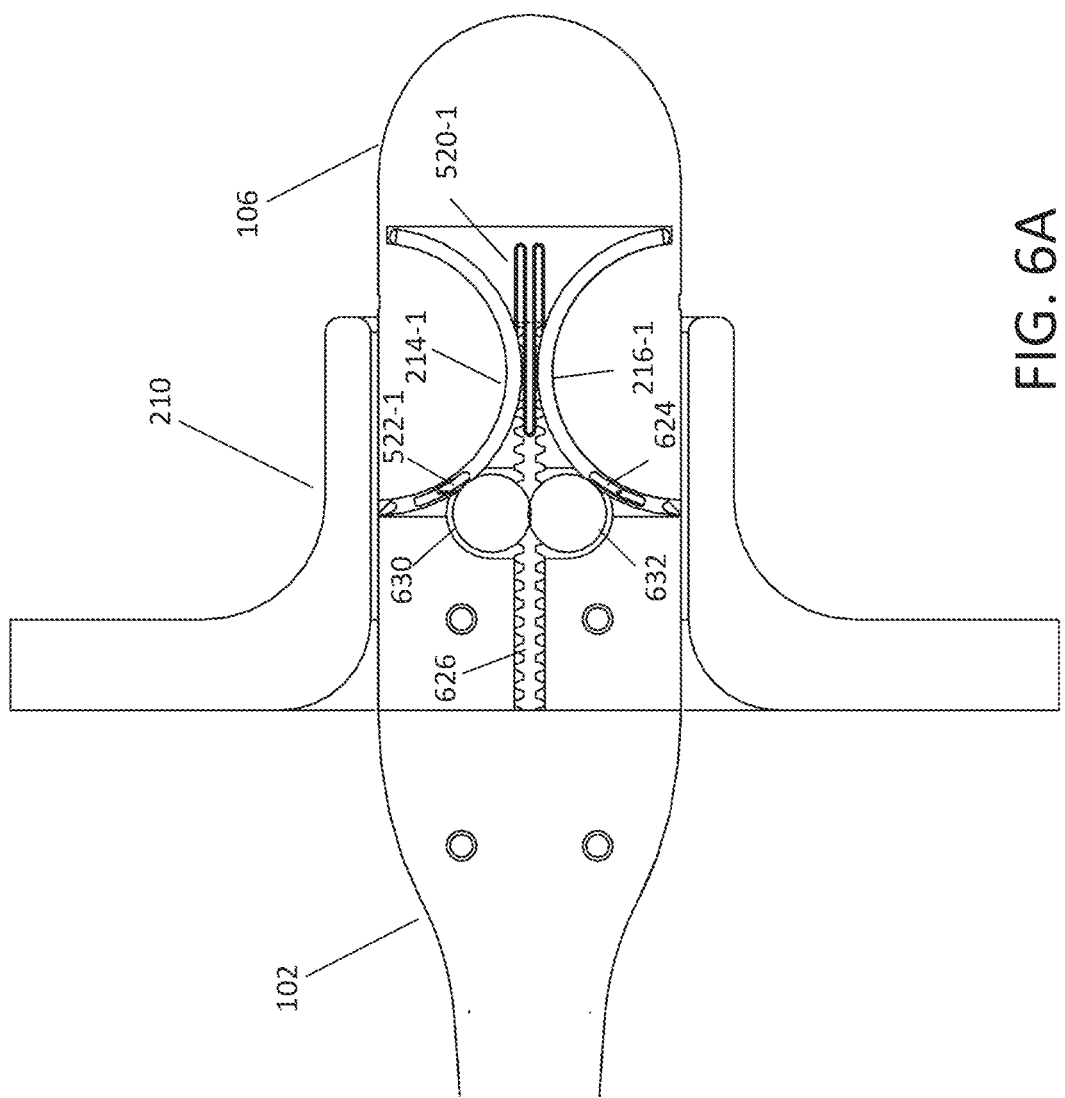

FIGS. 6A-6G illustrate a sectional view of suturing tissue using the suturing device 100 of FIG. 1A. Although FIGS. 6A-6G are discussed with respect to the curved needles 214-1 and 216-1, the discussion and FIGS. 6A-6G are applicable to any of the curved needles of the first set 214 and second set 216. FIG. 6A illustrates the suturing head 106 positioned in the separated vaginal cuff 210. The first anchor 522-1 is initially positioned within an aperture of the curved needle 214-1 and the second anchor 624-1 is initially positioned with an aperture of the curved needle 216-1. A portion of the suture 520-1 is bunched and/or wound between the curved needles 214-1 and 216-1 within the suturing head 106. The curved needle 214-1 rests against axle 630 in an interference fit. The curved needle 216-1 rests against axle 632 in an interference fit.

Figure 6B:
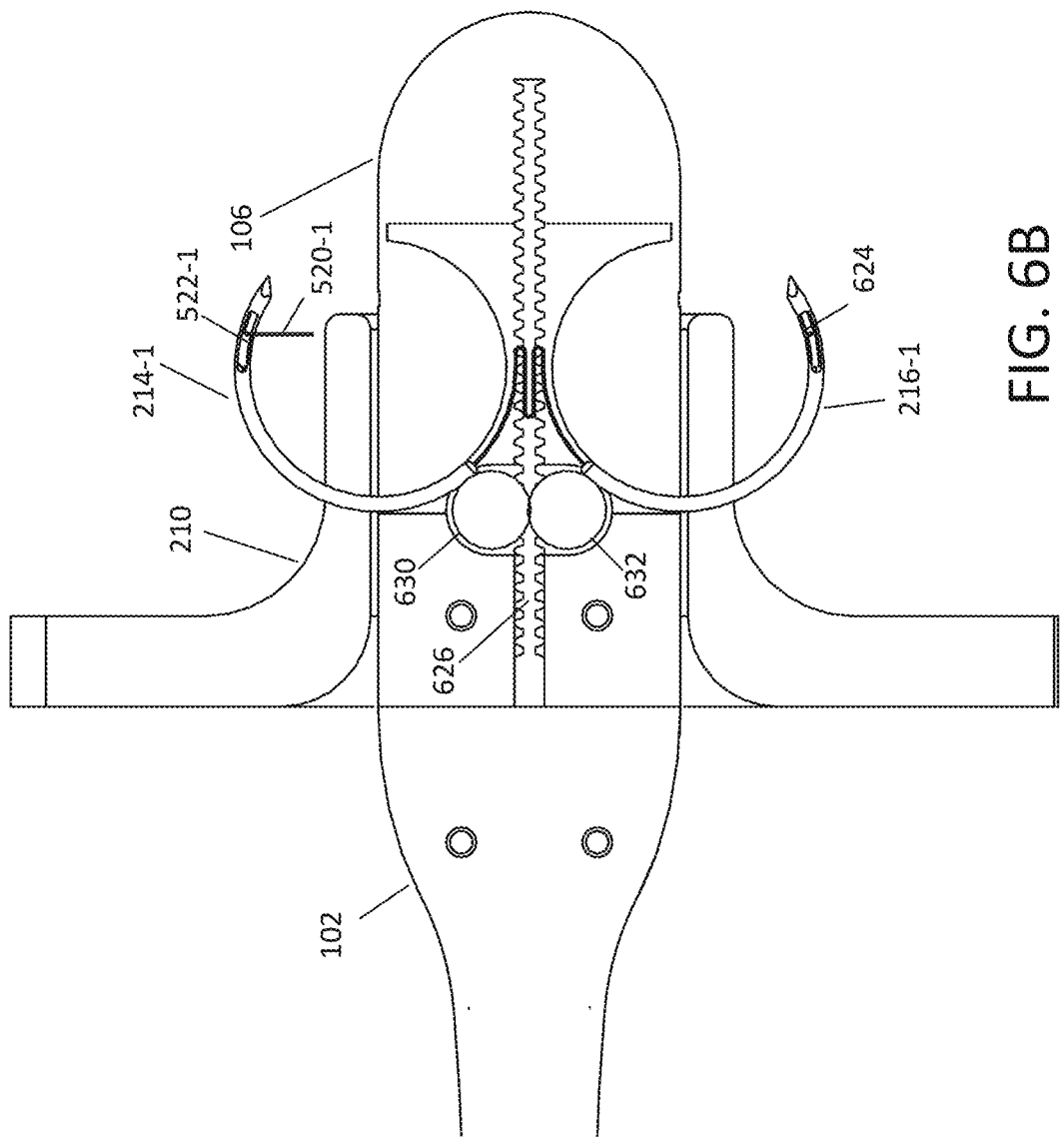

FIG. 6B illustrates deployment of the curved needles 214-1 and 216-1. The first anchor 522-1 and the second anchor 624-1 are still positioned in the apertures of the curved needles 214-1 and 216-1, respectively. As shown in FIG. 6B, the first anchor 522-1 is coupled to the suture 520-1 so that a first end of the suture 520-1 is free floating on one side of the first anchor 522-1. The second anchor 624-1 is fixedly coupled to a second end of the suture 520-1. In at least one embodiment, deploying the curved needle 214-1 includes rotating the curved needle 214-1 about a center point of the curved needle 214-1 and deploying the curved needle 216-1 includes rotating the curved needle 216-1 about a center point of the curved needle 216-1. As the curved needle 214-1 is deployed, the curved needle 214-1 passes through the anterior section of tissue of the separated vaginal cuff 210 and the curved needle 216-1 passes through the posterior section of tissue of the separated vaginal cuff 210.

Figure 6D:
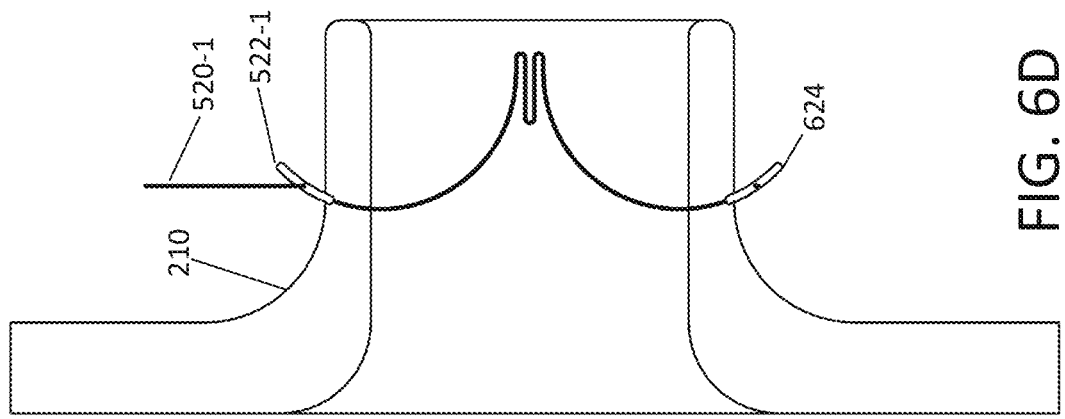

FIG. 6C illustrates the curved needles 214-1 and 216-1 retracted back into the suturing head 106, subsequent to deployment of the curved needles 214-1 and 216-1. As shown in FIG. 6C, retracting the curved needles 214-1 and 216-1 causes the first anchor 522-1 to separate from the curved needle 214-1 and the second anchor 624-1 to separate from the curved needle 216-1. Thus, the first anchor 522-1 and the second anchor 624-1 are positioned against the anterior and posterior sections of tissue of the vaginal cuff 210, respectively. FIG. 6D illustrates the first anchor 522-1 and the second anchor 624-1 positioned on an anterior and posterior surface of the separated vaginal cuff 210, respectively, after removal of the suturing head 106 from the vaginal cuff 210.

FIG. 6E illustrates the suture 520-1 in a tensioned state. Recall that the second end of the suture 520-1 is fixedly coupled to the second anchor 624-1. As tension is applied to the free floating portion of the suture 520-1, the bunched and/or wound portion of the suture 520-1 straightens as the suture 520-1 is pulled through the first anchor 522-1. The first anchor 522-1 traverses the suture 520-1 towards the second anchor 624-1 and the second anchor 624-1 is pulled towards the first anchor 522-1.

FIG. 6F illustrates the vaginal cuff 210 in a partially sutured and closed state. As additional tension is applied to the suture 520-1, the suture 520-1 passes through the first anchor 522-1. Because the second anchor 624-1 is fixedly coupled to the second end of the suture 520-1, the first anchor 522-1 traverses the suture 520-1 towards the second anchor 624-1. As a result, the first anchor 522-1 and/or the second anchor 624-1 apply a force to the anterior and posterior sections of tissue, respectively, to suture and close the separated vaginal cuff 210.

Figure 6G:
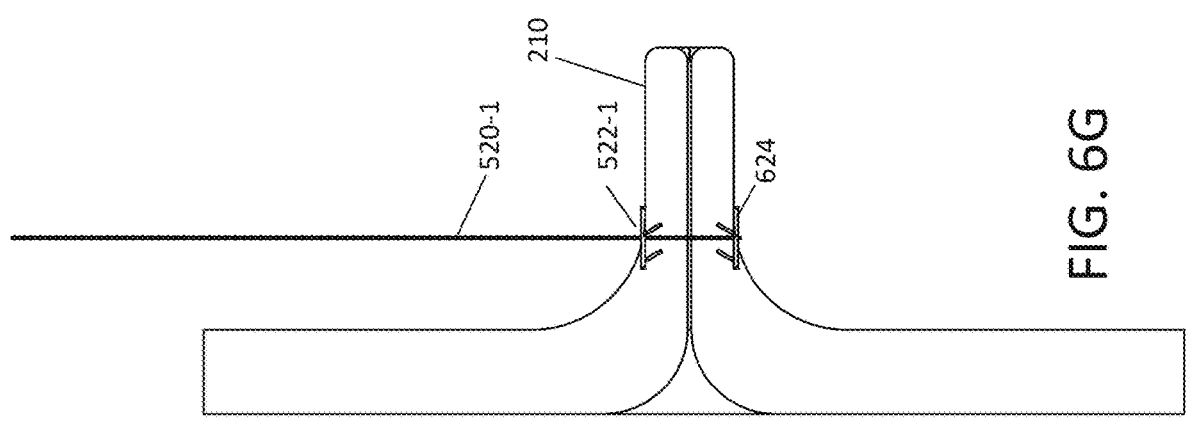

FIG. 6G illustrates the vaginal cuff 210 in a fully sutured and closed state. Tension is applied to the suture 520-1 until at least a portion of the anterior and posterior sections of tissues of the vaginal cuff 210 are in contact with each other. At this point, the free floating portion of the suture 520-1 on the side of the first anchor 522-1 can be trimmed and/or tied down to secure the position of the first anchor 522-1.

FIGS. 7A-7E illustrate the motion of curved needles the suturing device of FIG. 1A while suturing tissue. In FIGS. 7A-7E, the suturing head 106 is not shown only to clearly show the motion of the curved needles 214-1 and 216-1. Although FIGS. 7A-7E are discussed with respect to the curved needles 214-1 and 216-1, the discussion and FIGS. 7A-7E are applicable to any of the curved needles of the first set 214 and second set 216.

Figure 7A:
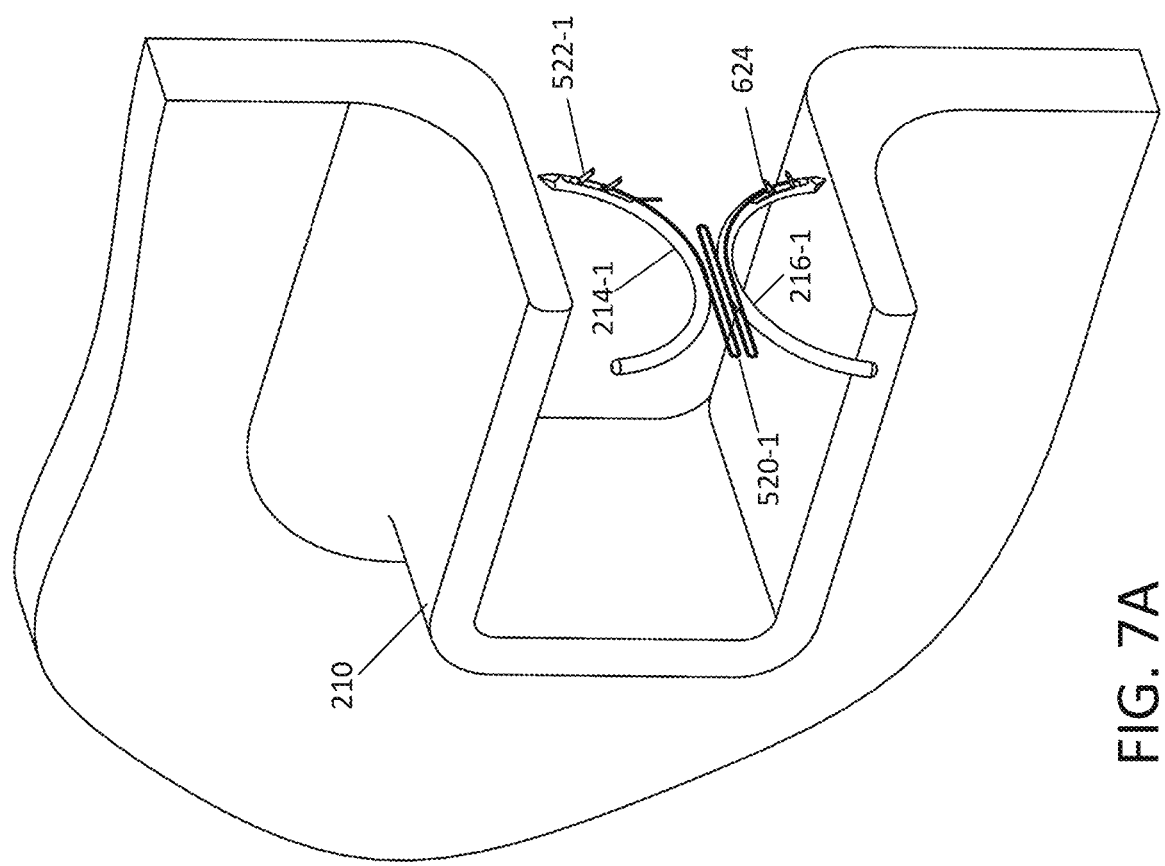
FIGS. 7A-7E illustrate the motion of curved needles the suturing device of FIG. 1A while suturing tissue.
Figure 7B:
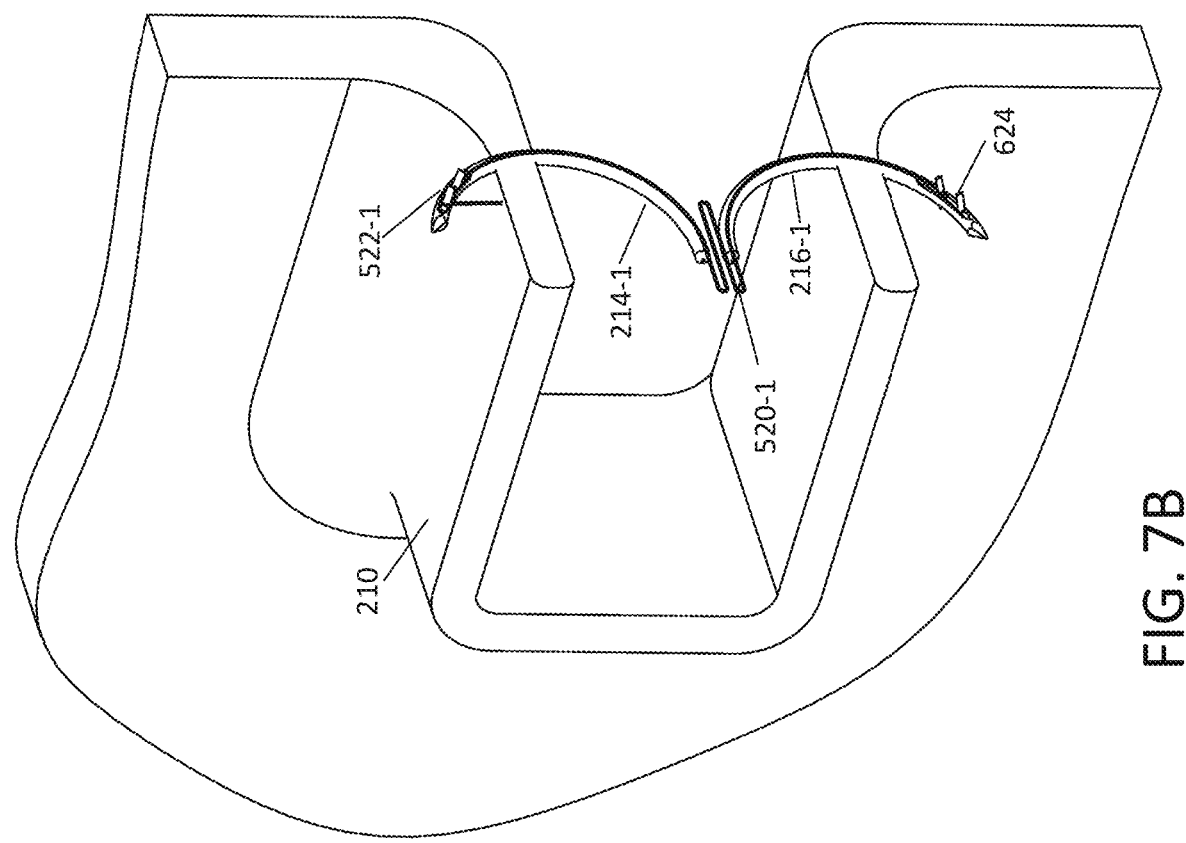
Figure 7C:
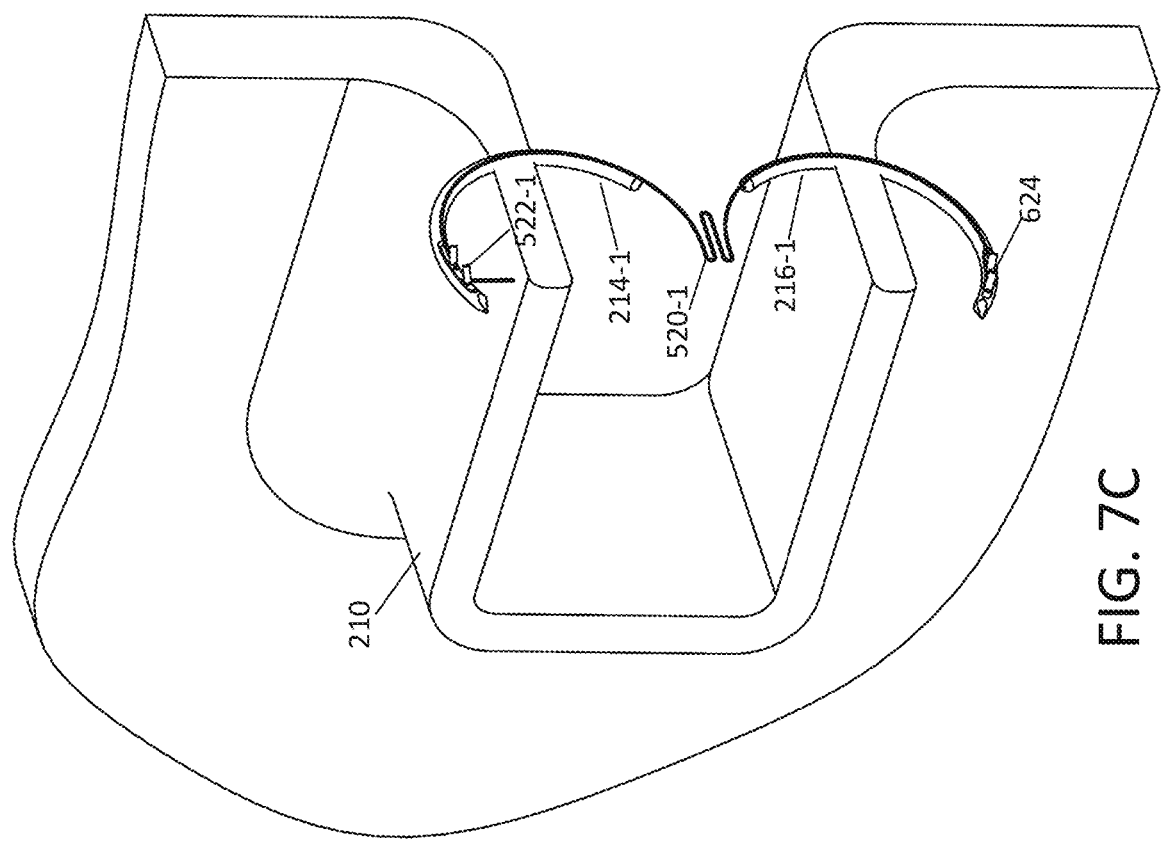

FIG. 7A illustrates the curved needles 214-1 and 216-1, the first anchor 522-1, the second anchor 624-1, and the suture 520-1 in their respective initial positions within the suturing head 106 (not shown). FIG. 7B illustrates partial deployment of the curved needles 214-1 and 216-1. FIG. 7C illustrates full deployment of the curved needles 214-1 and 216-1.

Figure 7D:
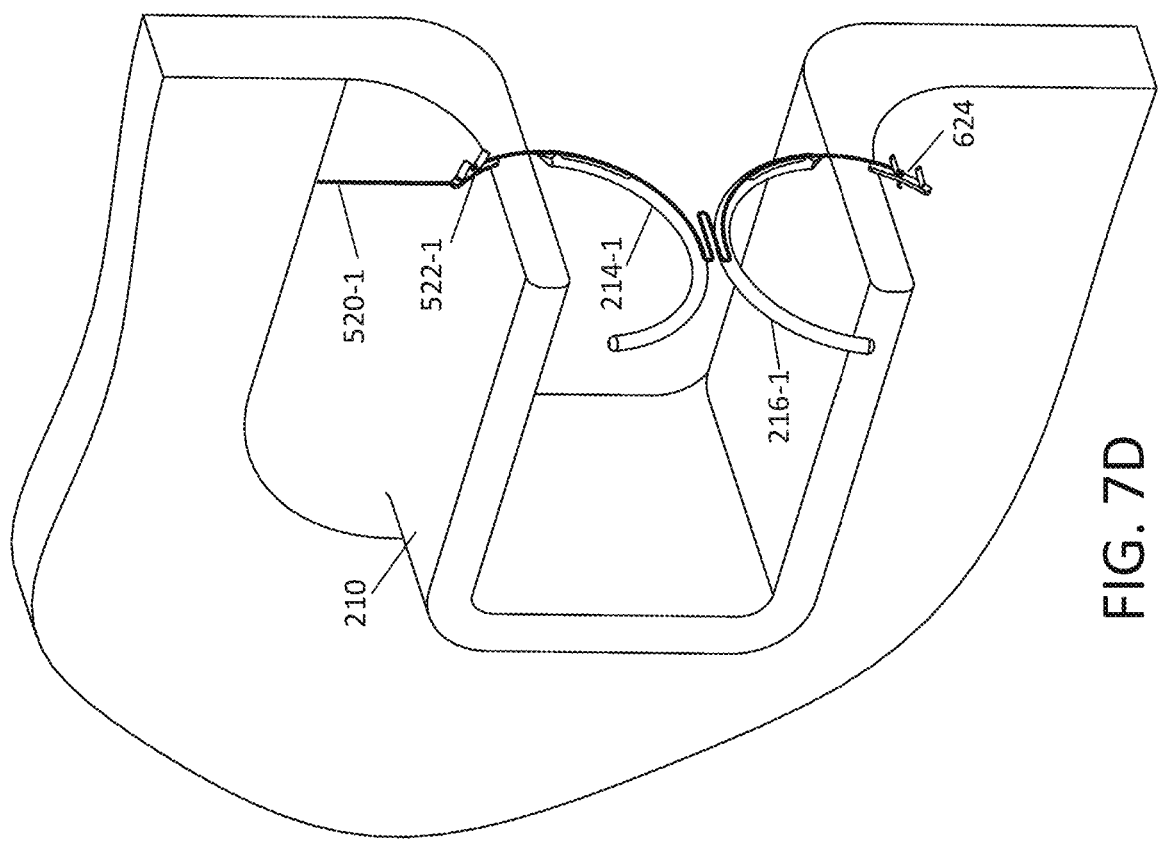
Figure 7E:
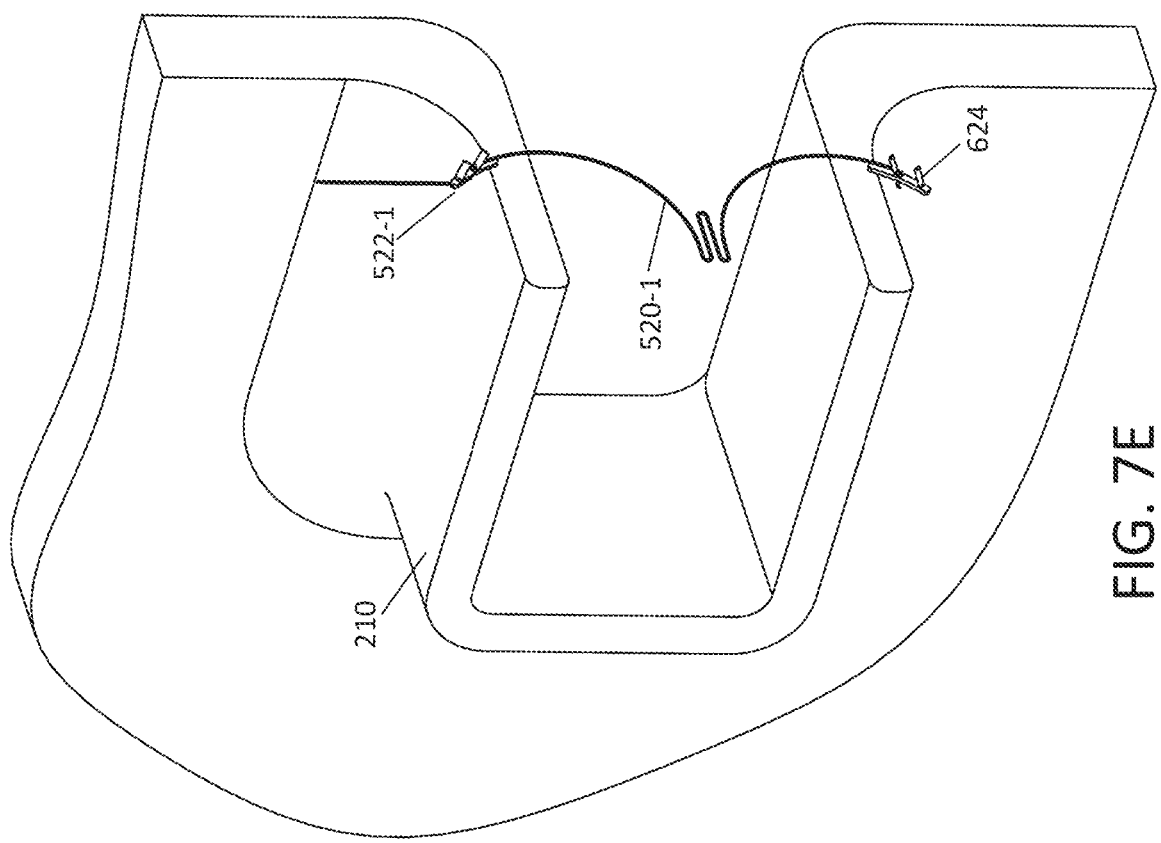

FIG. 7D illustrates the curved needles 214-1 and 216-1, the first anchor 522-1, the second anchor 624-1, and the suture 520-1 in their respective positions after the curved needles 214-1 and 216-1 are retracted back into the suturing head 106 (not shown). The first anchor 522-1 and the second anchor 624-1 have separated from the curved needles 214-1 and 216-1, respectively, and are positioned against the anterior and posterior sections of tissue of the vaginal cuff 210, respectively. FIG. 7E illustrates the first anchor 522-1, the second anchor 624-1, and the suture 520-1 in their respective positions after the suturing head 106 (not shown), including the curved needles 214-1 and 216-1, is removed from the vaginal cuff 210.

FIG. 8 is an exploded view of a curved needle 214-1, the first anchor 522-1, and the suture 520-1, in accordance with aspects of the present disclosure. Although FIG. 8 is discussed with respect to the curved needle 214-1, the first anchor 522-1, and the suture 520-1, the discussion and FIG. 8 are applicable to any of the curved needles, anchors, or sutures. The profile of the first anchor 522-1 is similar to the profile of the aperture 218 so that the first anchor 522-1 fits within the aperture 218. The first anchor 522-1 includes a plurality of tines 830. The tines 830 help maintain the position of the first anchor 522-1 against tissue. The first anchor 522-1 includes an aperture 832 through which the suture 520-1 can pass. The tines 830 cause the first anchor 522-1 to separate from the curved needle 214-1 as the curved needle 214-1 retracts back into the suturing head 106.

As shown in FIG. 8, the suture 520-1 can include a plurality of bumps (e.g., bump 834). In at least one embodiment, the suture 520-1 can be a barbed suture. The bumps enable the first anchor 520-1 to incrementally traverse the suture 520-1. In at least one embodiment, applying tension to the suture 520-1 includes ratcheting and/or cinching the first anchor 522-1 along the suture 520-1 towards the second anchor 624-1. In at least one embodiment, the suture 520-1 is a delayed absorbable suture.

Figure 10:
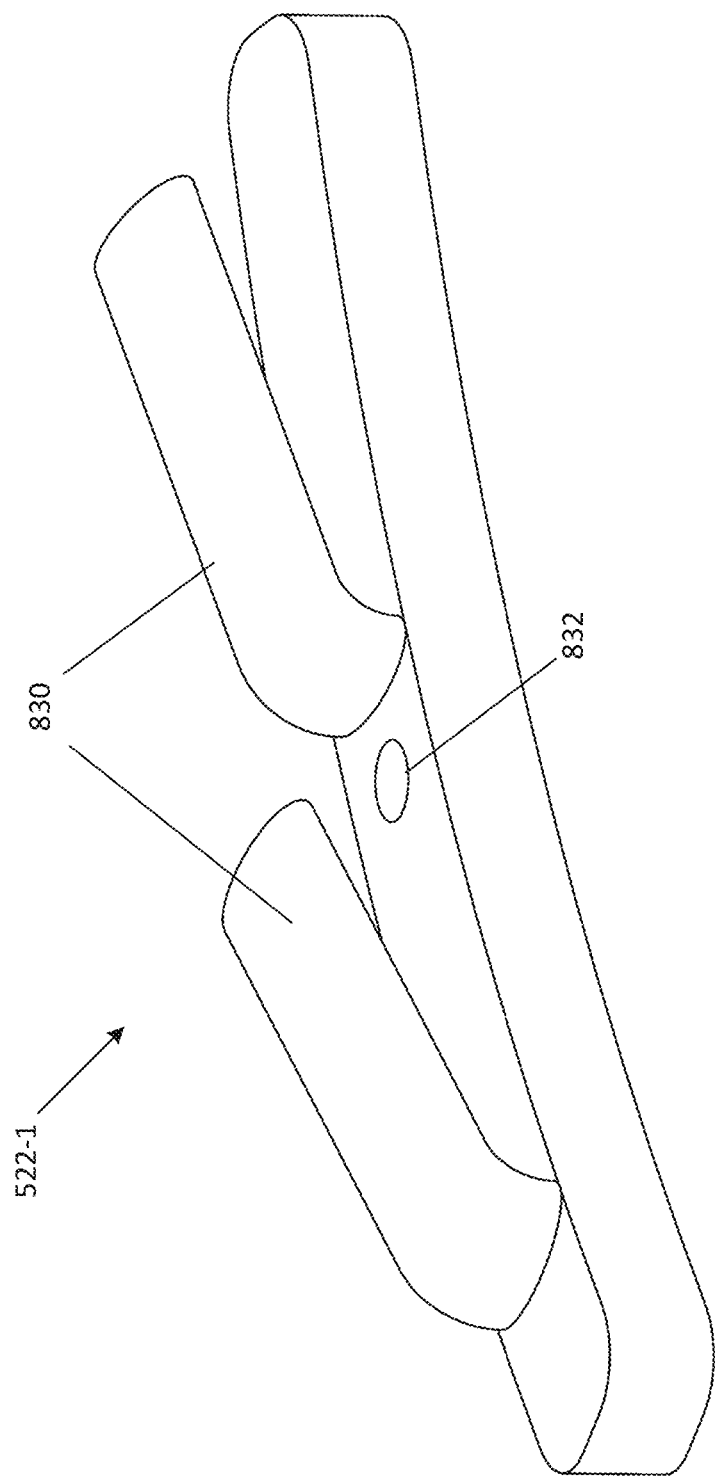
FIG. 10 is a view of the anchor of FIG. 9 with flexed tines.

FIG. 9 is a view of the first anchor 522-1, in accordance with aspects of the present disclosure. Although FIG. 9 is discussed with respect to the first anchor 522-1, the discussion and FIG. 9 are applicable to any of the anchors. The first anchor 522-1 includes an aperture 832 through which the suture 520-1 can pass. The first anchor 522-1 includes a plurality of tines 830. The tines 830 help maintain the position of the first anchor 522-1 against tissue by flexing. FIG. 10 is a view of the anchor of FIG. 9 with the tines 830 flexed.

Figure 11:
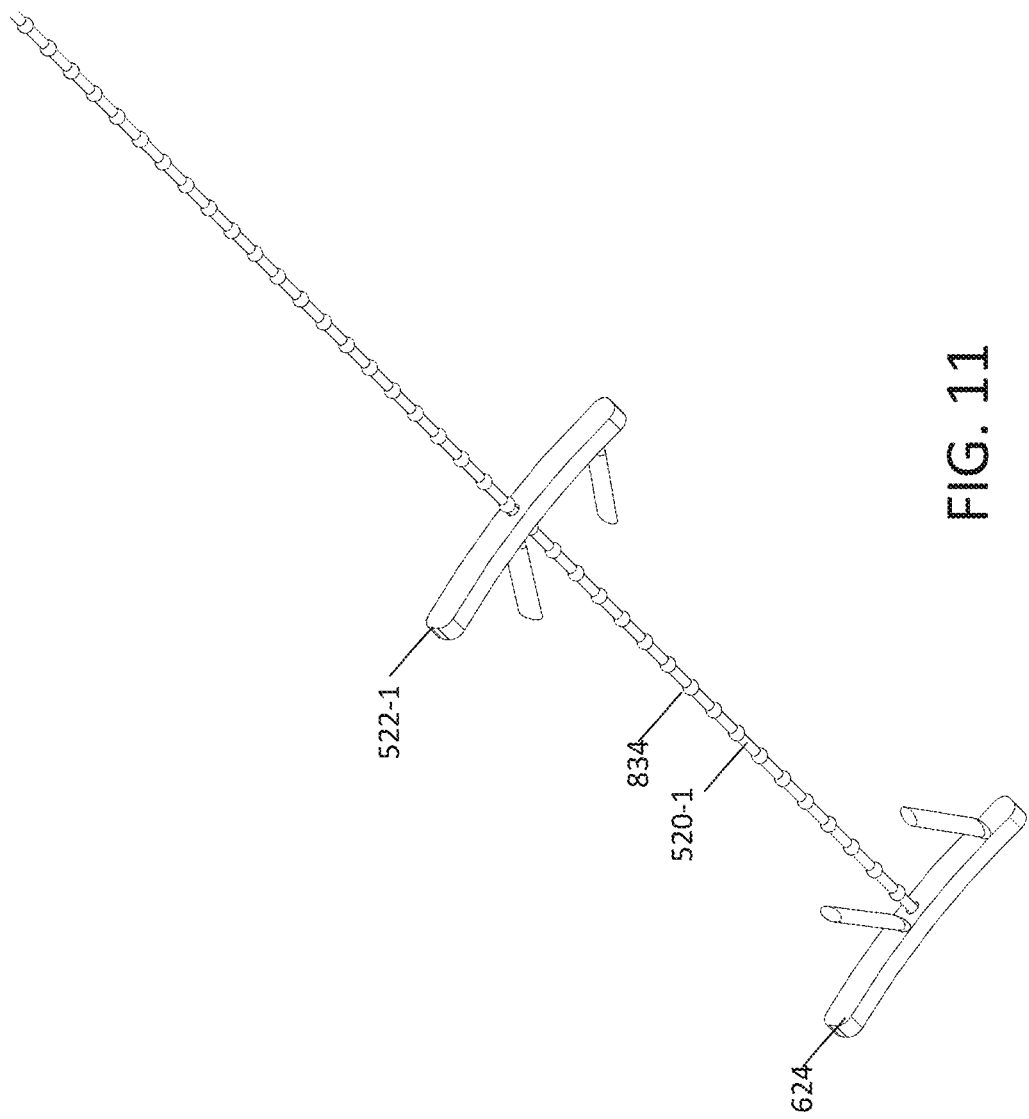
FIG. 11 is a view of a pair of anchors coupled to a suture, in accordance with aspects of the present disclosure.

FIG. 11 is a view of a pair of anchors coupled to a suture, in accordance with aspects of the present disclosure. Although FIG. 11 is discussed with respect to the first anchor 522-1, the second anchor 624-1, and the suture 520-1, the discussion and FIG. 11 are applicable to any pair of first and second anchors coupled to a suture. As shown in FIG. 11, the second anchor is fixedly coupled to an end of the suture 520-1 whereas the first anchor 522-1 is slidably coupled to the suture 520-1. The plurality of bumps, including the bump 834, on the suture 520-1 inhibit the traversal of the first anchor 522-1 along the suture 520-1.

Figure 12:
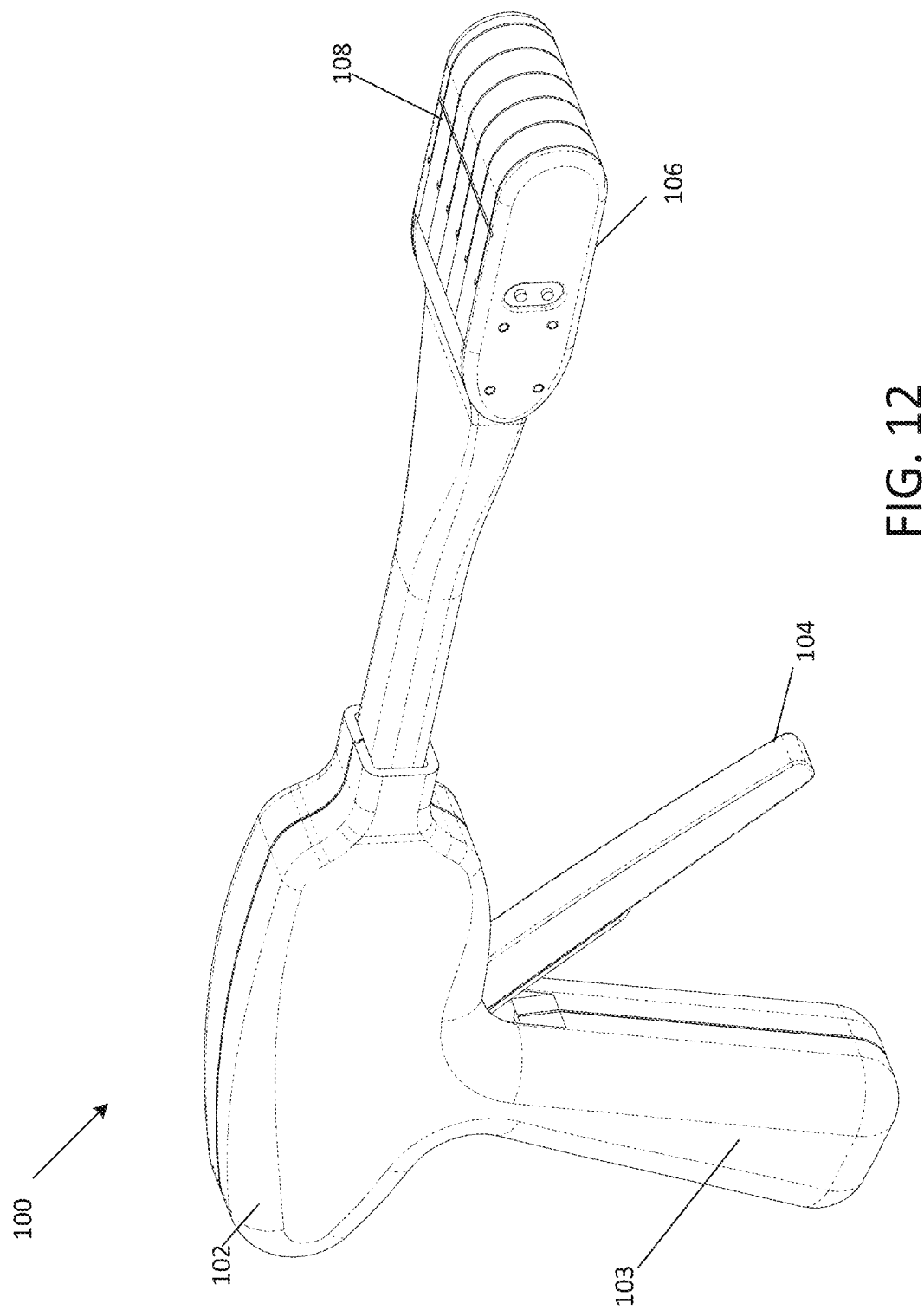
FIG. 12 is a view of the tissue suturing device of FIG. 1A.
Figure 13:
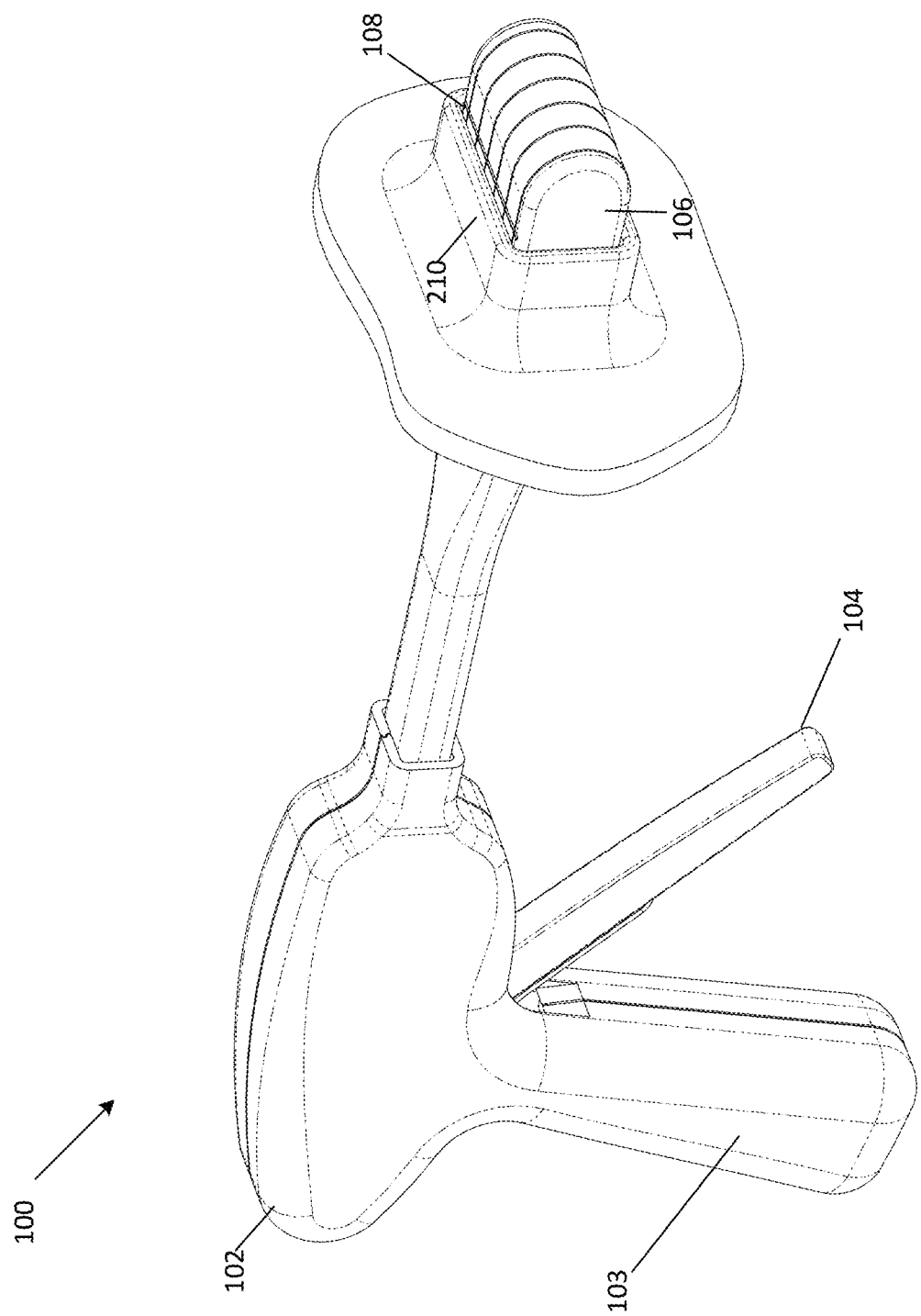
FIG. 13 is a view of the tissue suturing device of FIG. 1A aligned in a separated vaginal cuff.
Figure 14:
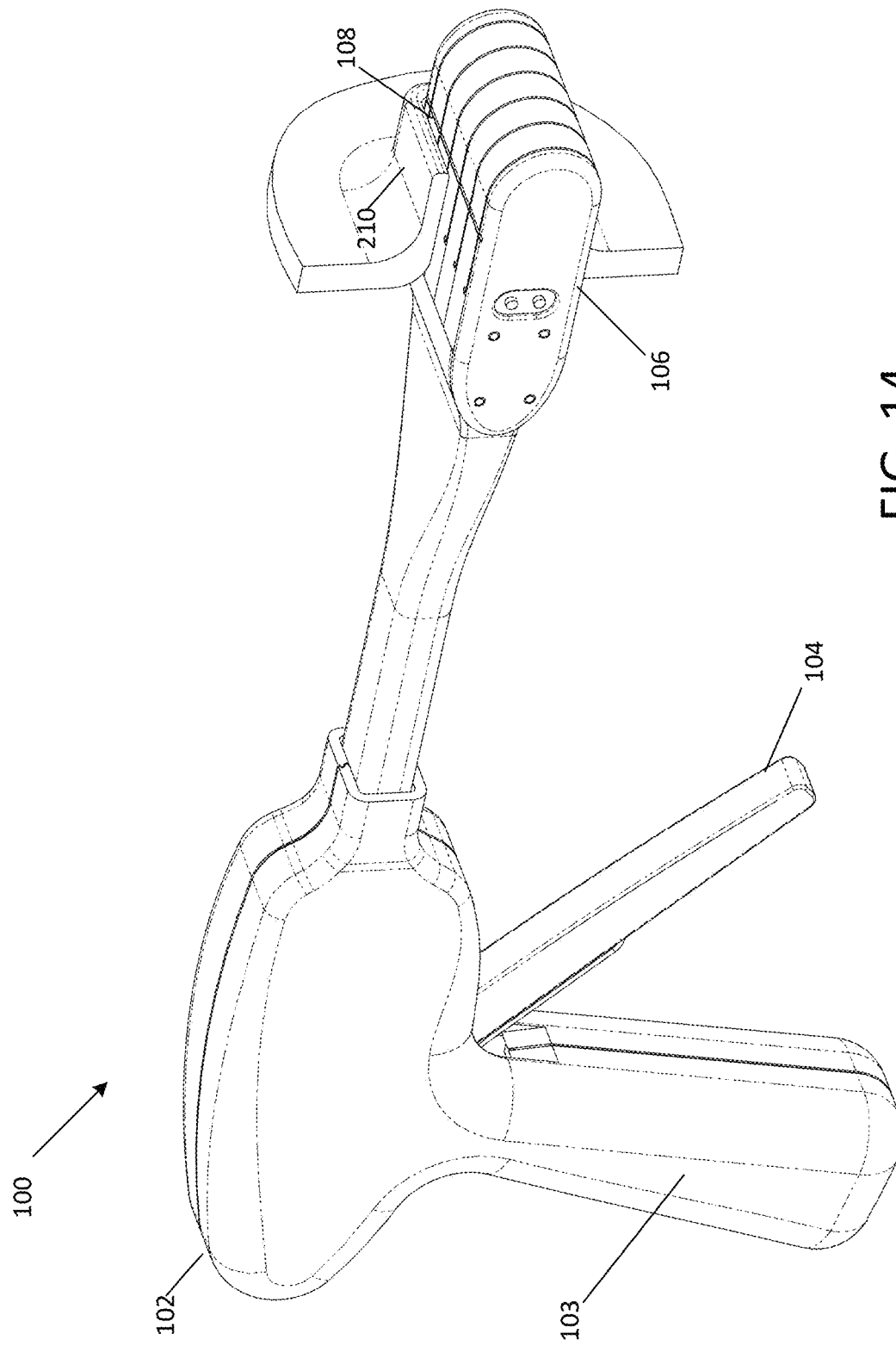
FIG. 14 is a view of the tissue suturing device of FIG. 1A aligned in a sectional view of a separated vaginal cuff.
Figure 15:
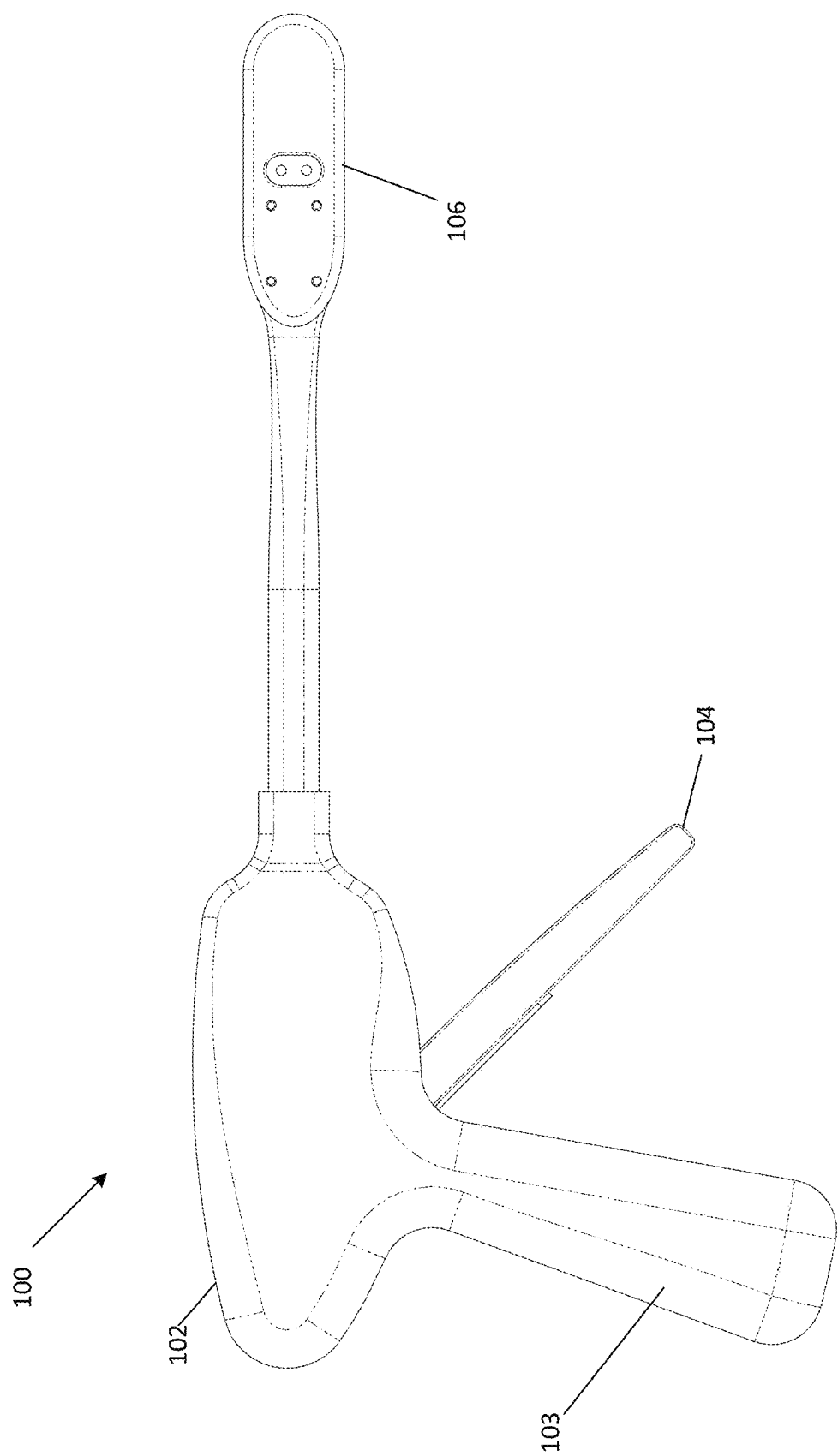
FIG. 15 is a view of the tissue suturing device of FIG. 1A.

FIG. 12 is a view of the tissue suturing device 100 of FIG. 1A. FIG. 13 is a view of the tissue suturing device 100 of FIG. 1A aligned in a separated vaginal cuff 210. FIG. 14 is a view of the tissue suturing device 100 of FIG. 1A aligned in a sectional view of a separated vaginal cuff 210. FIG. 15 is a side view of the tissue suturing device 100 of FIG. 1A.

Figure 16:
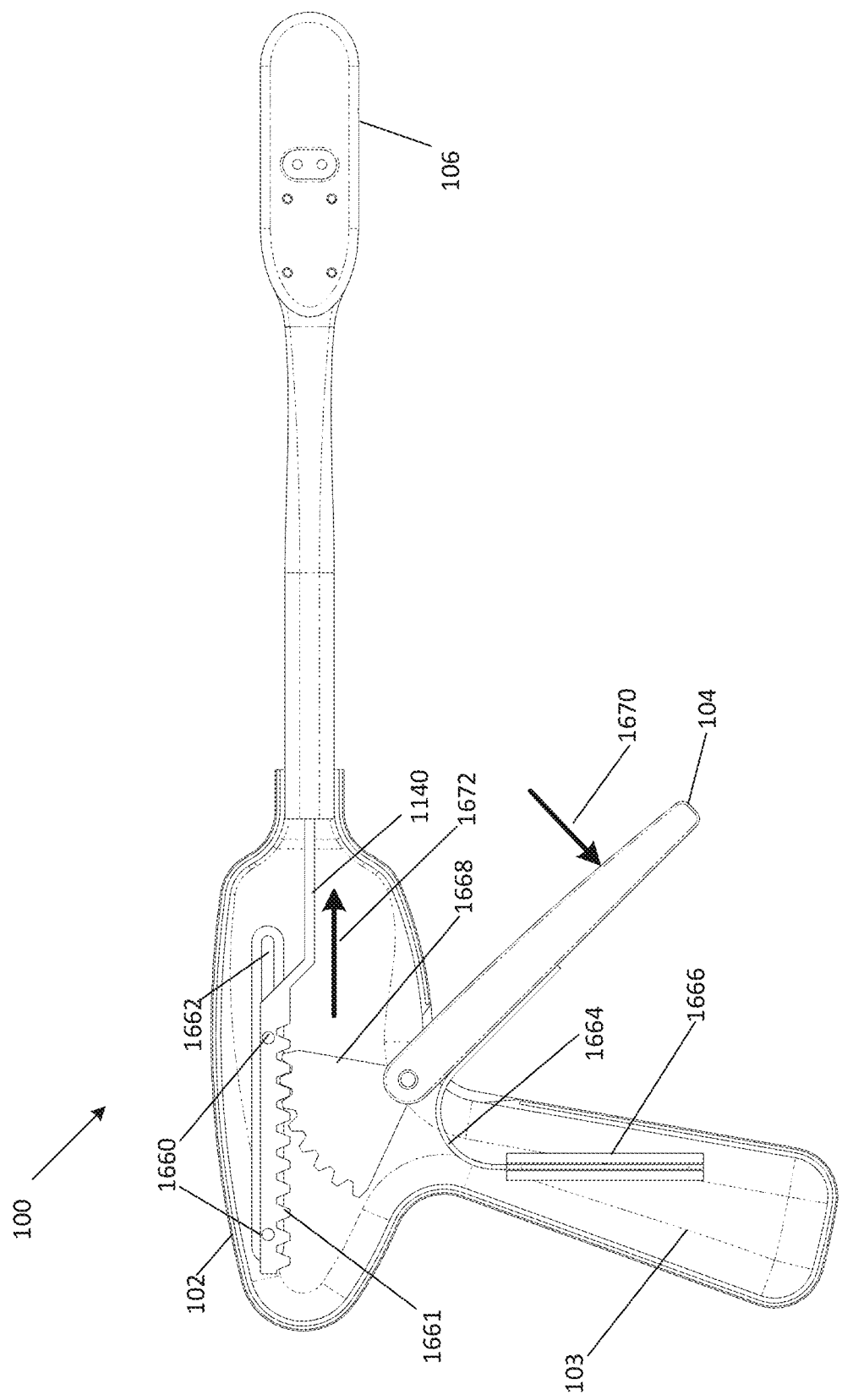
FIG. 16 is a sectional view of the handle of the tissue suturing device of FIG. 1A.

FIG. 16 is a sectional view of the handle 103 of the tissue suturing device 100 of FIG. 1A. The trigger 104 is coupled to a gear 1668 and a spring 1664. An end of the spring 1664 is coupled to the handle 103 by being positioned in a slot 1666 of the handle 103. As a result, the trigger 104 is a spring-load trigger such that pulling the trigger 104 deploys the first and second sets of curved needles from the suturing head 106. When the trigger 104 is released, the spring 1664 forces the trigger 104 back to an initial state so that the first and second sets of curved needles retract back into the suturing head 106.

Pulling the trigger 104 causes the gear 1668 to push elongated member 1140 toward the suturing head 106, as indicated by the arrow 1672, via a gear track 1661. The elongated member 1140 includes a plurality of pins 1660 positioned in a slot 1662 of the body 102. The pins 1660 and slot 1662 cooperate to control the motion of the elongated member 1140.

Figure 17:
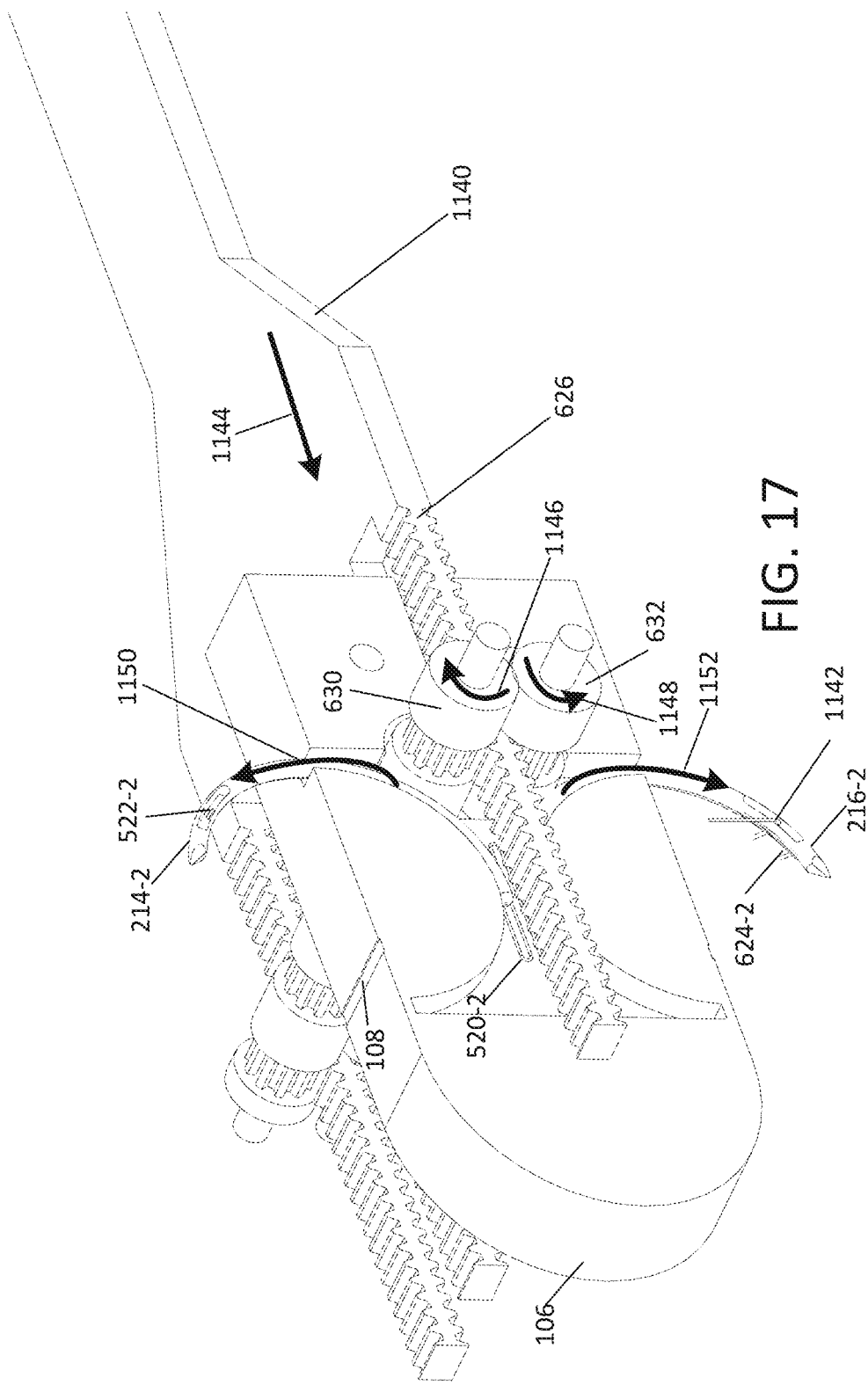
FIG. 17 is a view of components of the suturing head of the tissue suturing device of FIG. 1A.

FIG. 17 is a view of components of the suturing head 106 of the tissue suturing device 100 of FIG. 1A. The elongated member 1140 includes a plurality of racks 626 (also shown in FIGS. 6A-6C). The racks 626 include a gear track on each of a respective upper surface and a respective lower surface on a distal prong of the elongated member 1140. In some implementations, the quantity of prongs can be equal to the quantity of curved needles in each of the first and second sets. The racks 626 are coupled to the axles 630 and 632 via pinions (gears) on each of the axles 630 and 632.

Pulling the trigger 104 (not shown) causes the elongated member 1140 and the racks 626 to move distally as indicated by the arrow 1144. The motion of the racks 626 causes the axle 630 to rotate in a first direction (clockwise from the perspective of FIG. 17) as indicated by the arrow 1146. Because the curved needle 214-2 is in an interference fit with the axle 630, the rotation of the axle 630 in the first direction causes the curved needle 214-2 to rotate in a second direction (counterclockwise from the perspective of FIG. 17) opposite to the first direction as indicated by the arrow 1150. Thus, the rotation of the axle 630 in the first direction deploys the curved needles of the first set 214 (only the curved needle 214-2 is shown for clarity).

The motion of the racks 626 as indicated by the arrow 1144 causes the axle 632 to rotate in the second direction (counterclockwise from the perspective of FIG. 17) as indicated by the arrow 1148. Because the curved needle 216-2 is in an interference fit with the axle 632, the rotation of the axle 632 in the second direction causes the curved needle 216-2 to rotate in the first direction (clockwise from the perspective of FIG. 17) as indicated by the arrow 1152. Thus, the rotation of the axle 632 in the second direction deploys the curved needles of the second set 216 (only the curved needle 216-2 is shown for clarity). Note that the axles 630 and 632 rotate simultaneously so that the curved needles of the first set 214 and the second set 216 deploy simultaneously.

Releasing the trigger 104 causes the elongated member 1140 and the racks 626 to move proximally, opposite to the direction indicated by the arrow 1144. The motion of the racks 626 causes the axles 630 and 632 to rotate in directions opposite to those indicated by the arrows 1146 and 1148. Because the curved needles 214-2 and 216-2 are in an interference fit with the axles 630 and 632, respectively, the rotation of the axles 630 and 632 in directions opposite to those indicated by the arrows 1146 and 1148 causes the curved needles 214-2 and 216-2 to rotate in directions opposite to that indicated by the arrows 1150 and 1152. Thus, the rotation of the axles 630 and 632 retract the curved needles of the first set 214 and the second set 216 back into the suturing head 106. Note that the axles 630 and 632 rotate simultaneously so that the curved needles of the first set 214 and the second set 216 retract simultaneously.

Figure 18:
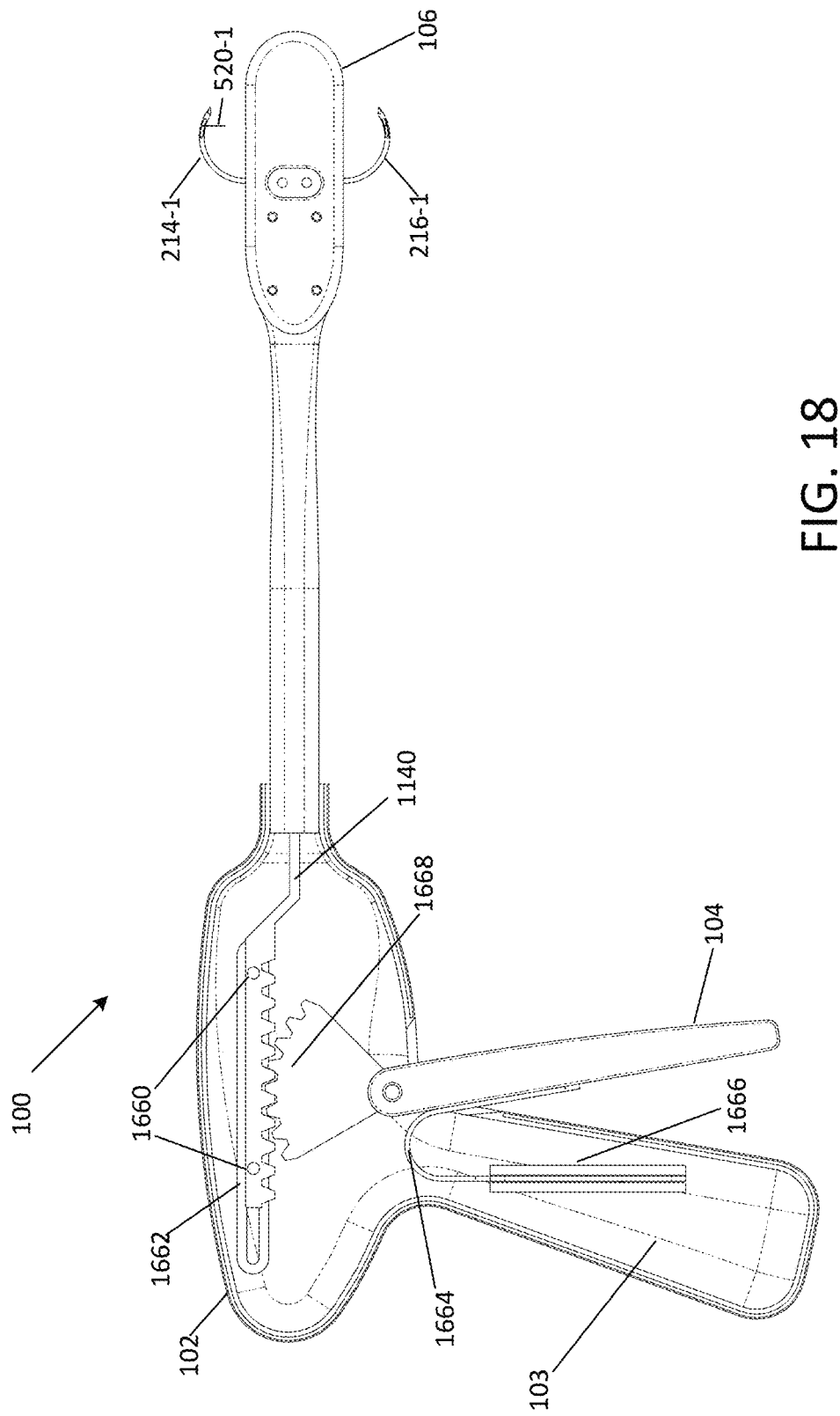
FIG. 18 is a sectional view of the handle of the tissue suturing device of FIG. 1A with curved needles deployed.

FIG. 18 is a sectional view of the handle 103 of the tissue suturing device 100 of FIG. 1A with the curved needles 214-1 and 216-1 deployed.

Figure 19:
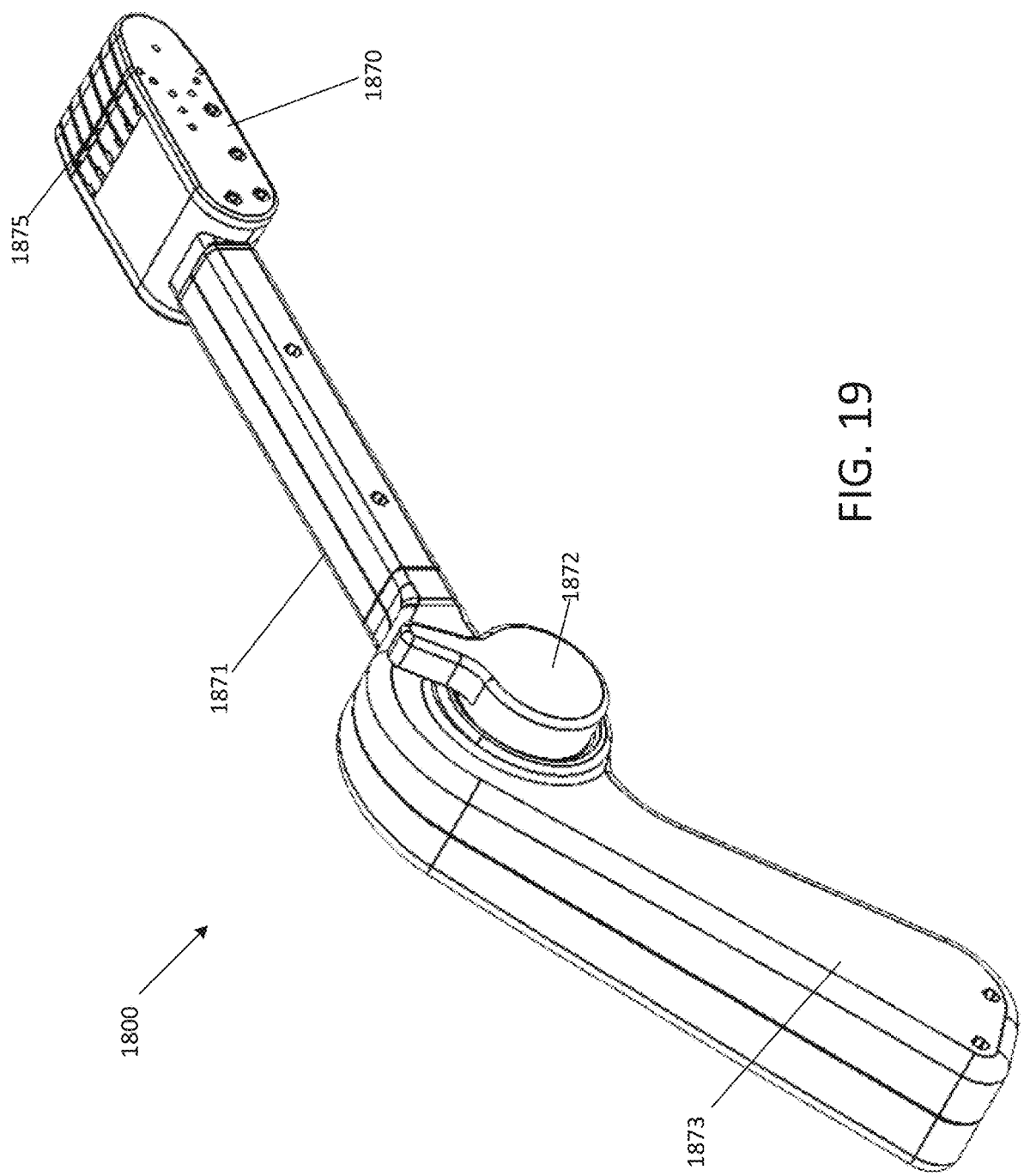
FIG. 19 is a view of a tissue suturing device, in accordance with aspects of the present disclosure.
Figure 20:
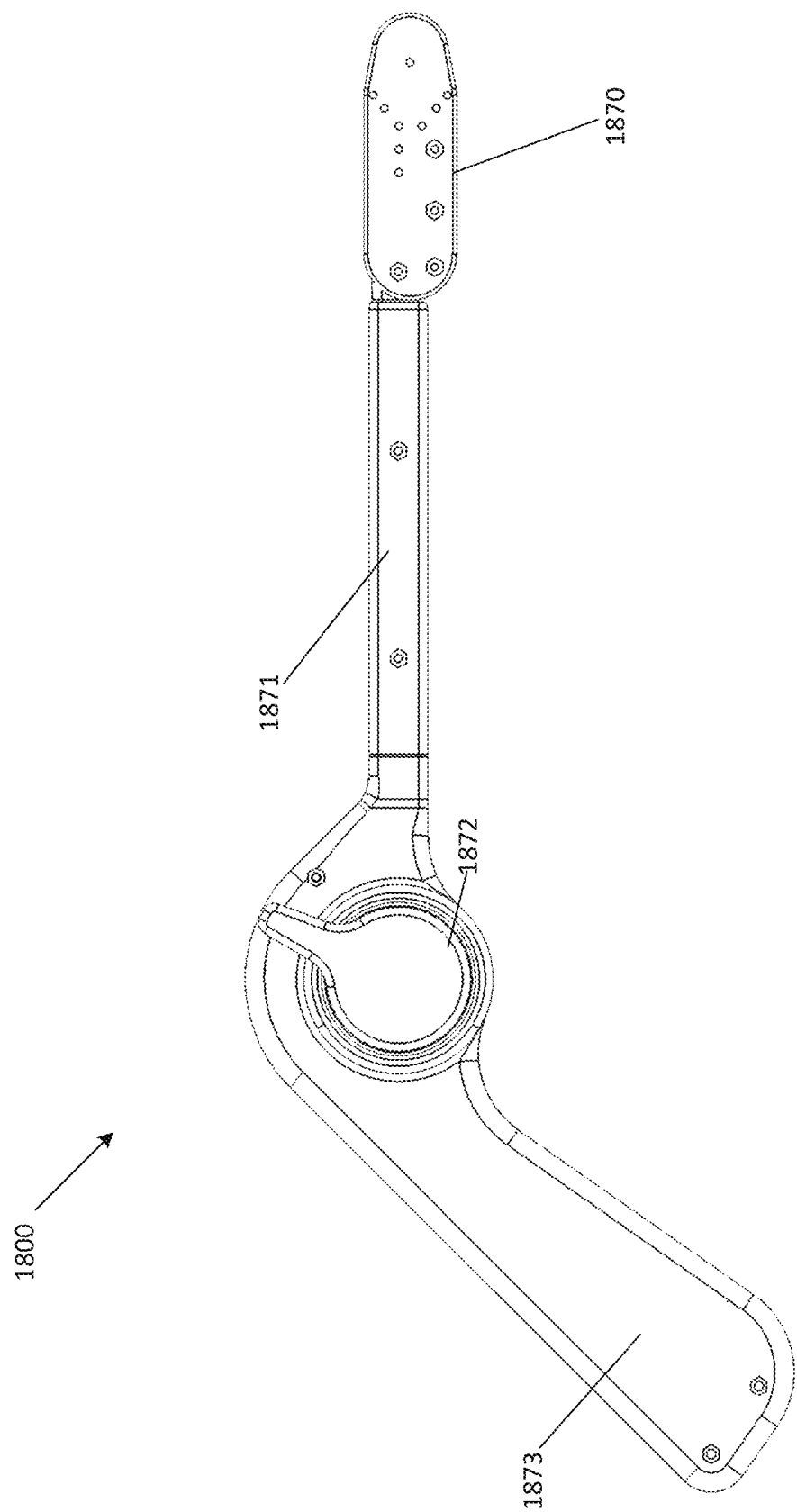
FIG. 20 is a side view of the tissue suturing device of FIG. 19.

FIG. 19 is a view of a tissue suturing device 1800, in accordance with aspects of the present disclosure. The tissue suturing device 1800 includes a body 1871 having a distal end and a proximal end. A suturing head 1870 is coupled to the distal end of the body 1871. The suturing head 1870 can be inserted into the vagina. The suturing head 1870 includes at least one alignment marking 1875 to aide in aligning the suturing head 1870 with the tissue to be sutured. For example, the alignment marking can position curved needles of the suturing head 1870 ten millimeters (mm) from an edge of the vaginal cuff 210. Examples of the alignment marking 1875 include, but are not limited to, a radiopaque marking, a fluoroscopic marking, and an indentation. A handle 1873 is coupled to the proximal end of the body 1871. A knob 1872 is coupled to the handle 1873 and/or the body 1871. The knob 1872 can deploy curved needles from the suturing head 1870, which is discussed further in association with FIGS. 21-24 below. FIG. 20 is a side view of the tissue suturing device 1800 of FIG. 19.

Figure 21:
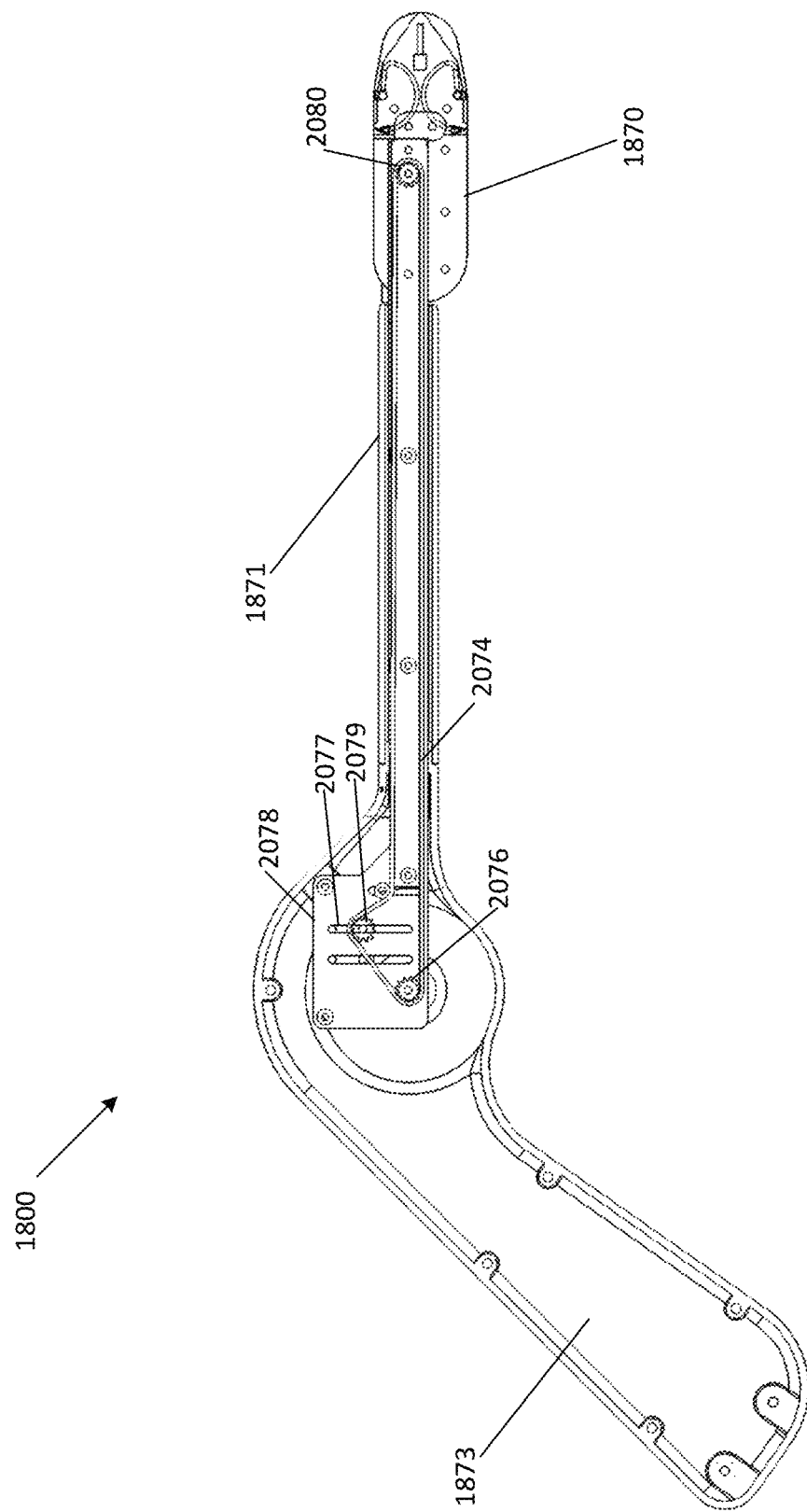
FIG. 21 is a sectional view of the tissue suturing device of FIG. 19.

FIG. 21 is a sectional view of the tissue suturing device 1800 of FIG. 19. The knob 1872 (not shown) is coupled to a gear 2076. The gear 2076 is coupled to a toothed belt 2074. The belt 2074 is coupled to a gear 2080 of the suturing head 1870 and a gear 2079. The gear 2079 is coupled a slot 2077 in a frame 2078. In at least one embodiment, the position of the gear 2079 in the slot 2077 is adjustable so that the tension in the belt 2074 can be adjusted.

Figure 22:
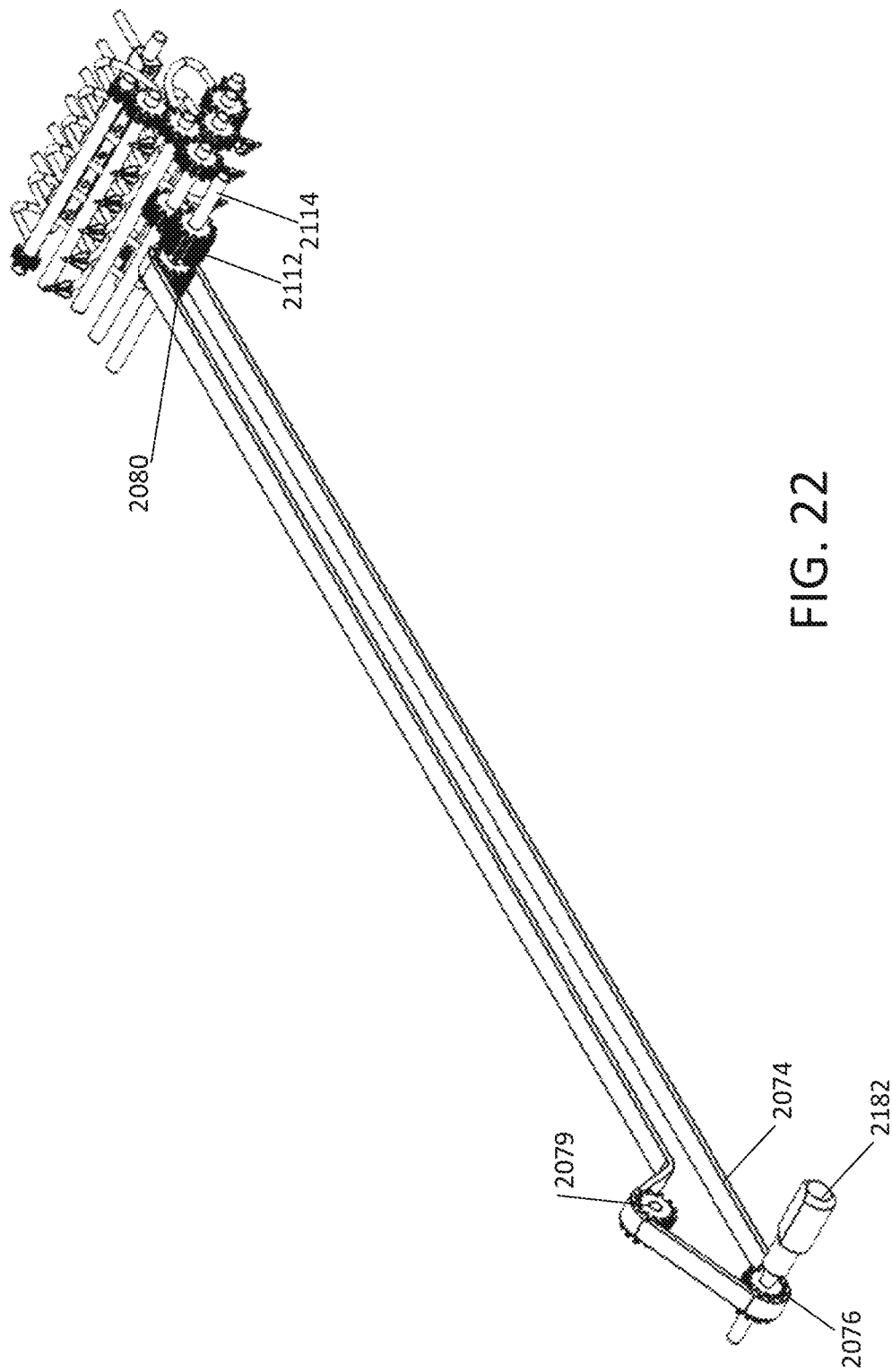
FIG. 22 is a view of components of the tissue suturing device of FIG. 19.

FIG. 22 is a view of components of the tissue suturing device 1800 of FIG. 19. In FIG. 22, other components of the tissue suturing device 1800, including the body 1871 and the knob 1872, are not shown for clarity. The gear 2076 is coupled to the knob 1872 by a shaft 2182. The shaft 2182 includes a flat portion to maintain an orientation of the knob 1872 relative to the shaft 2182. The gear 2080 is coupled to a gear 2112 by a shaft 2114.

Figure 23:
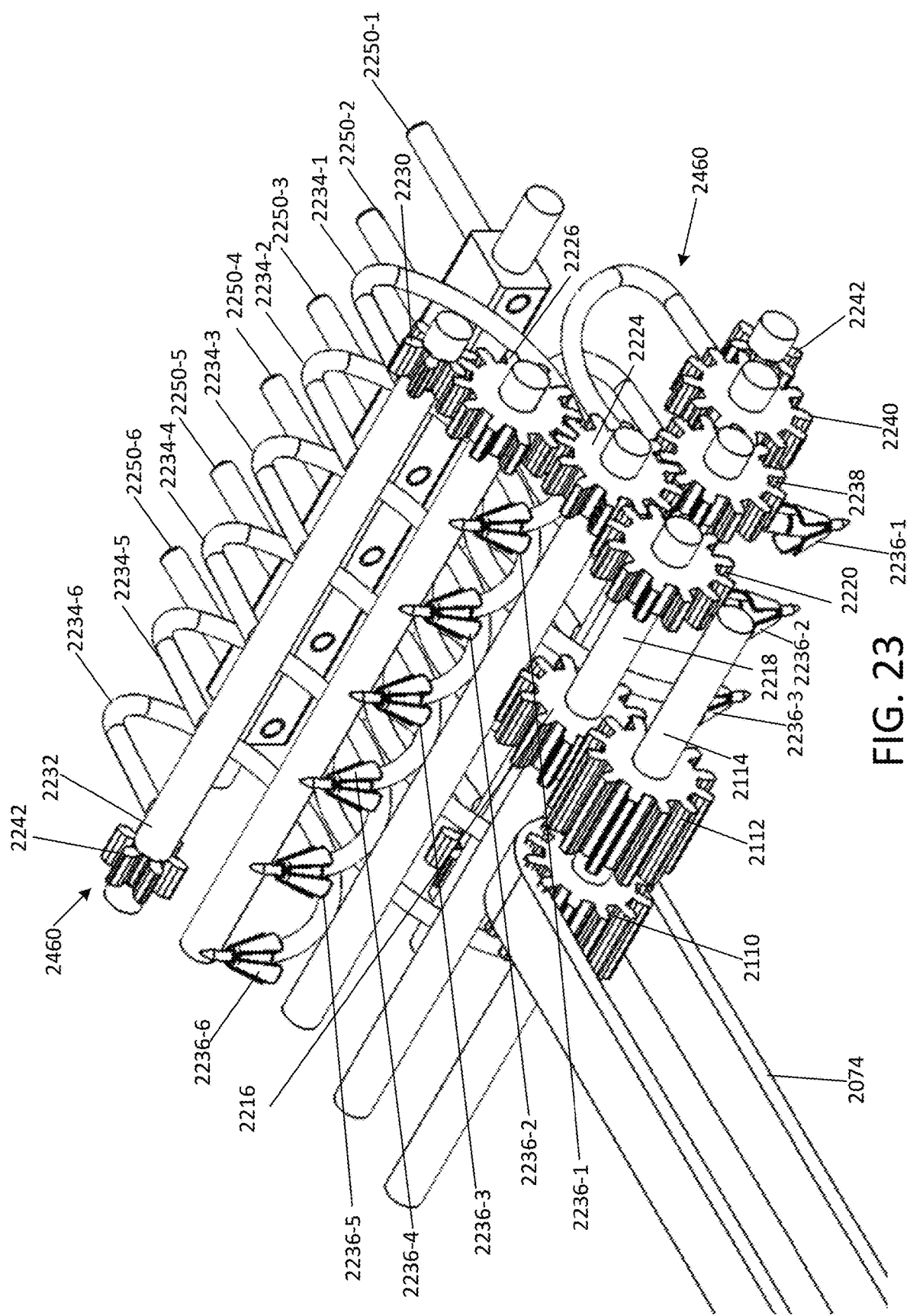
FIG. 23 is a view of components of a suturing head of the tissue suturing device of FIG. 19.

FIG. 23 is a view of components of the suturing head 1870 of the tissue suturing device 1800 of FIG. 19. The gear 2112 is coupled to a gear 2116. The gear 2116 is coupled to a gear 2220 by a shaft 2218. The gear 2220 is coupled to the gear 2224. The gear 2224 is coupled to gears 2226 and 2238. The gear 2226 is coupled to a gear 2230 of an axle 2232 of a first instance of a set of curved needles 2460. The set 2460 includes the curved needles 2234-1, 22234-2, 2234-3, 2234-4, 2234-5, and 2234-6 (collectively referred to as the curved needles 2234). The curved needles 2234 are coupled to the axle 2232. Each of the curved needles 2234 is coupled to a respective one of anchors 2236-1, 2236-2, 2236-3, 2236-4, 2236-5, and 2236-6 (collectively referred to as the anchors 2236). Each of the anchors 2236 are coupled to a suture (not shown).

The gear 2240 is coupled to a gear 2242 of a second instance of the set of curved needles 2460. The second instance is the same as the first instance but the first instance is driven by the gear 2230 on the axle 2232 whereas the second instance is driven by the gear 2242 on the axle 2232.

Rotating the knob 1872 causes rotation of the gears 2110, 2112, 2116, 2220, 2224, 2226, 2230, 2238, 2240, and 2242. Rotating the knob 1872 in a first direction causes rotation of the gear 2230 driven by the gear 2226, which causes the curved needles 2234 of the first instance of the set 2460 to rotate about the axle 2232 (clockwise from the perspective of FIG. 23), thereby deploying the needles of the first instance of the set 2460. Rotating the knob 1872 in the first direction causes rotation of the gear 2242 driven by the gear 2240, which causes the curved needles 2234 of the second instance of the set 2460 to rotate about the axle 2232 (counterclockwise from the perspective of FIG. 23), thereby deploying the needles of the second instance of the set 2460. Note that because the gear 2224 drives both the gears 2226 and 2238, the axle 2232 of both the first and second instances of the set 2460 rotate simultaneously so that the curved needles deploy simultaneously.

Rotating the knob 1872 in a second direction, opposite to the first direction, causes rotation of the gear 2230 driven by the gear 2226, which causes the curved needles 2234 of the first instance of the set 2460 to rotate about the axle 2232 (counterclockwise from the perspective of FIG. 23), thereby retracting the needles of the first instance of the set 2460. Rotating the knob 1872 in the second direction causes rotation of the gear 2242 driven by the gear 2240, which causes the curved needles 2234 of the second instance of the set 2460 to rotate about the axle 2232 (clockwise from the perspective of FIG. 23), thereby retracting the needles of the second instance of the set 2460. Note that because the gear 2224 drives both the gears 2226 and 2238, the axle 2232 of both the first and second instances of the set 2460 rotate simultaneously so that the curved needles retract simultaneously.

Figure 24:
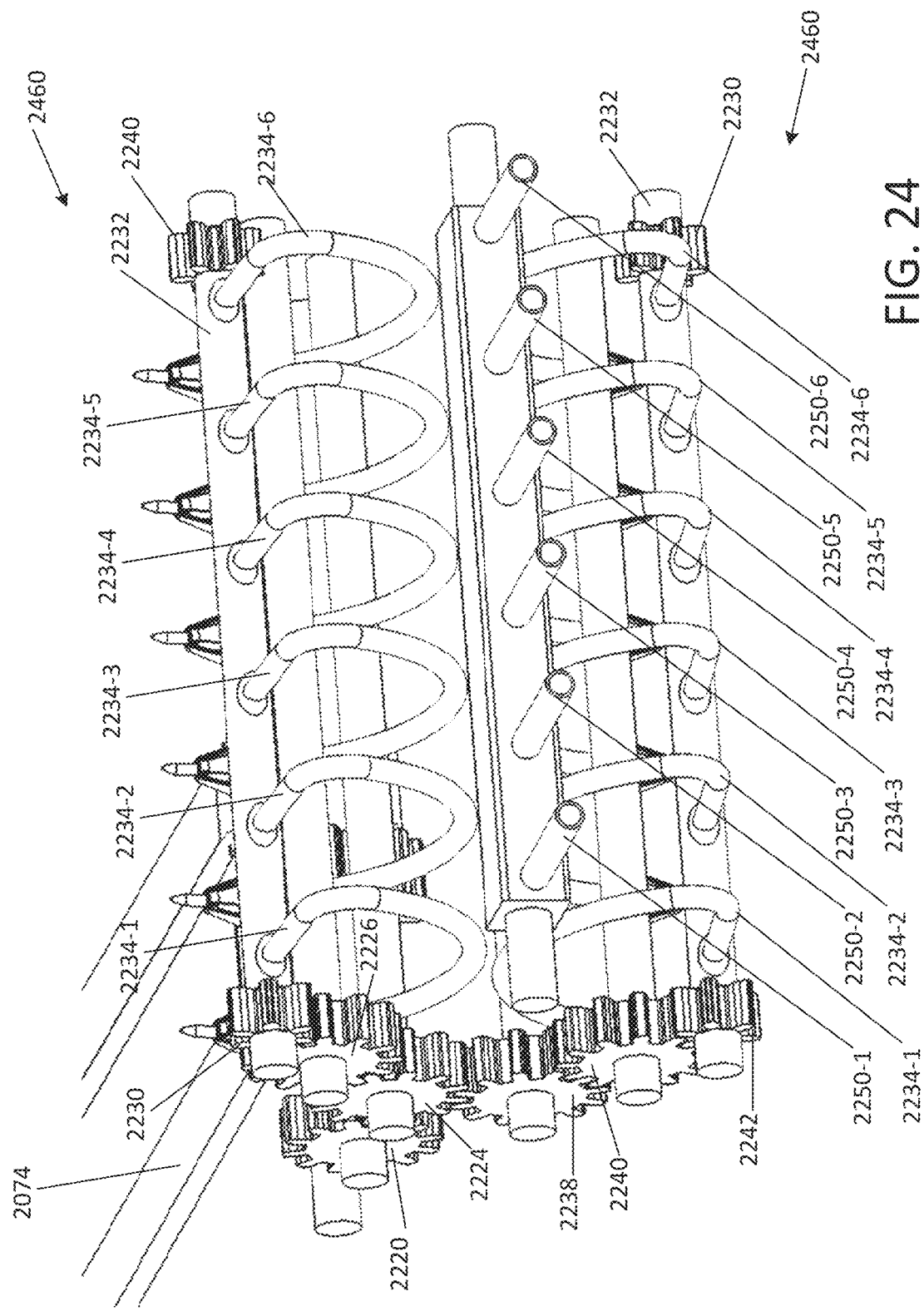
FIG. 24 is an end view of components of a suturing head of the tissue suturing device of FIG. 19.

The suturing head 1870 includes a plurality of suture feeding tubes 2250-1, 2250-2, 2250-3, 2250-4, 2250-5, and 2250-6 (collectively referred to as the suture feeding tubes 2250). The suturing head 1870 is not removably coupled to the body 1871. Thus, the suturing head 1871 has to be loaded with sutures prior to each use. The sutures are fed through the suture feeding tubes 2250. After feeding the sutures, each of the sutures are coupled to an anchor (e.g. the anchor 2236-1) of the first instance of the set 2460 and an anchor (e.g. the anchor 2236-1) of the second instance of the set 2460. FIG. 24 is an end view of components of the suturing head 1870 of the tissue suturing device 1800 of FIG. 19.

Figure 25:
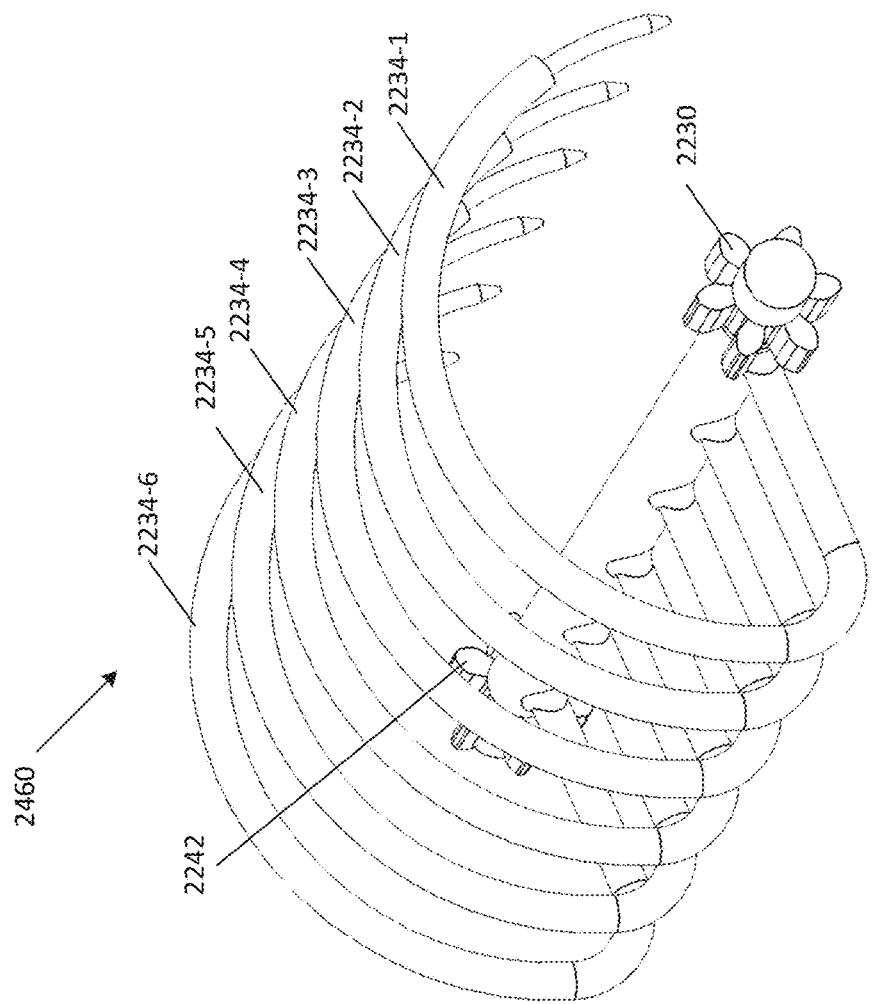
FIG. 25 is a view of a set of curved needles, in accordance with aspects of the present disclosure.

FIG. 25 is a view of a set of curved needles 2460, in accordance with aspects of the present disclosure. The set 2460 is used as both the first instance and the second instance of the set 2460 (e.g., first and second sets of curved needles). Each of the curved needles 2234 include a first, relatively proximal region having a first diameter and a second, relatively distal region having a second diameter. The distal region includes a distal tip of each one of the curved needles 2234. The second diameter is smaller than the first diameter. One of the anchors 2236 can be coupled to each of the curved needles 2234 in the distal region.

Figure 26A:
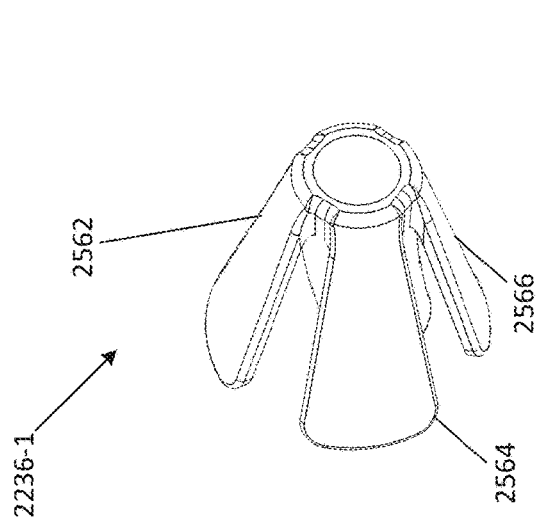
FIGS. 26A-26B are views of an anchor, in accordance with aspects of the present disclosure.
Figure 26B:
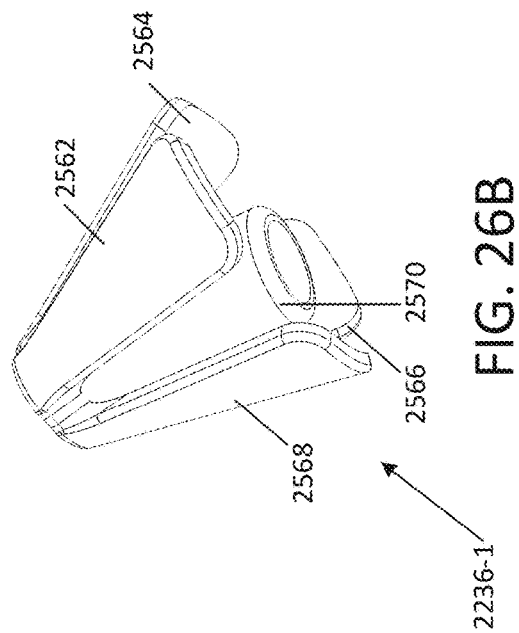

FIGS. 26A-26B are views of the anchor 2236-1, in accordance with aspects of the present disclosure. Although FIGS. 26A-26B are discussed with respect to the anchor 2236-1, the discussion and FIGS. 26A-26B are applicable to any of the anchors 2236. The anchor 2236-1 includes four tines 2562, 2564, 2566, and 2568. The anchor 2236-1 includes a central portion 2570 that has a profile and/or curvature similar to the distal portion of the curved needles 2234. As the curved needles 2234 are deployed, the anchors 2236 pass through sections of tissue with the curved needles 2234. As the curved needles 2234 retract back into the suturing head 1870, the tines 2562, 2564, 2566, and 2568 cause the anchors 2236 separate from the curved needles 2234.

The embodiments described with respect to FIGS. 19-25B can suture tissue, such as a separated vaginal cuff, as described with respect to FIGS. 1-18. The anchors 2236 of the first instance of the set of curved needles 2460 (e.g., a first set of curved needles) can be analogous to the first anchors 522. The anchors 2236 of the second instance of the set of curved needles 2460 (e.g., a second set of curved needles) can be analogous to the second anchors, such as the second anchor 624-1'.

It will be apparent to those skilled in the art that various modifications and variations can be made in the disclosed devices and methods without departing from the scope of the disclosure. While a variety of devices and methods have been made and used for suturing tissue, it is believed that no one prior to Applicant has made or used the technology described herein. Other aspects of the disclosure will be apparent to those skilled in the art from consideration of the specification and practice of the features disclosed herein. It is intended that the specification and examples be considered as exemplary only.

What is claimed is:

1. A method of suturing tissue, comprising:
   positioning a first set of needles and a second set of needles between first and second substantially parallel sections of tissue, wherein the first set of needles are oppositely oriented to the second set of needles, and wherein first portions of a set of sutures are respectively coupled to the first set of needles, and second portions of the set of sutures are respectively coupled to the second set of needles;
   deploying the first and second sets of needles, such that the first set of needles, along with the first portions of the set of sutures, pass through the first section of tissue and exit at a first set of exit points, and the second set of needles, along with the second portions of the set of sutures, pass through the second section of tissue and exit at a second set of exit points;
   retracting the first and second sets of needles through the respective first and second set of exit points, such that the first portions of the set of sutures decouple from the first set of needles and, after retracting the first set of needles, extend through the first set of exit points, and the second portions of the set of sutures decouple from the second set of needles and, after retracting the second set of needles, extend through the second set of exit points; and
   tensioning the set of sutures to suture the first and second sections of tissue together.

2. The method of claim 1, wherein the first and second sections of tissue form a tissue cuff.

3. The method of claim 2, wherein the tissue cuff includes a separated vaginal cuff, the first section of tissue is an anterior section of the separated vaginal cuff, and the second section of tissue is a posterior section of the separated vaginal cuff.

4. The method of claim 1, wherein a first set of anchors are respectively coupled to the first portions of the set of sutures and to the first set of needles, and a second set of anchors are respectively coupled to the second portions of the set of sutures and to the second set of needles;
   wherein the first and second sets of needles are deployed, such that the first set of needles, along with the first set of anchors, pass through the first section of tissue and exit at the first set of exit points, and the second set of needles, along with the second set of anchors, pass through the second section of tissue and exit at the second set of exit points;
   wherein the first and second sets of needles are retracted from between the first and second sections of tissue, such that the first set of anchors decouple from the first set of needles and, after retracting the first set of needles, extend through the first set of exit points, and the second set of anchors decouple from the second set of needles and, after retracting the second set of needles, extend through the second set of exit points; and
   wherein tensioning the set of sutures includes respectively advancing the first set of anchors along the set of sutures towards the second set of anchors to force the first and second sections of tissue together.

5. The method of claim 4, wherein the first set of anchors are slidably coupled to the first portions of the set of sutures, such that free ends of the set of sutures are free floating on one side of the first set of anchors, and the second set of anchors are fixedly coupled to the second portions of the set of sutures, wherein tensioning the set of sutures includes pulling on the free ends of the set of sutures, such that the first set of anchors are advanced along the set of sutures towards the second set of anchors to force the first and second sections of tissue together.

6. The method of claim 4, wherein the needles of the first set of needles respectively comprise a first set of apertures in which the first set of anchors are respectively positioned, and the needles of the second set of needles respectively comprise a second set of apertures in which the second set of anchors are respectively positioned.

7. The method of claim 4, wherein each needle of the first and second sets of needles includes:
   a first, relatively proximal region having a first diameter; and
   a second, relatively distal region having a second diameter, the distal region including a distal tip of the needle, wherein the second diameter is smaller than the first diameter; and
   wherein the first set of anchors are respectively coupled to the distal regions of the first set of needles, and the second set of anchors are respectively coupled to the distal regions of the second set of needles.

8. The method of claim 1, wherein each needle of the first and second sets of needles is a curved needle, wherein deploying the first and second sets of curved needles includes rotating the first set of curved needles in a first direction about a first axis, and wherein rotating the second set of curved needles in a second direction, opposite to the first direction, about a second axis.

9. The method of claim 8, wherein retracting the first and second sets of curved needles includes rotating the first set of curved needles in the second direction about the first axis, and rotating the second set of curved needles in the first direction about the second axis.

10. The method of claim 8, wherein each curved needle of the first and second sets of needles is an arcuate needle.

11. The method of claim 1, wherein deploying the first and second sets of needles includes simultaneously deploying the first and second sets of needles, and wherein retracting the first and second sets of needles includes simultaneously retracting the first and second sets of needles.

12. A method of suturing tissue, comprising:
    positioning a first set of needles and a second set of needles adjacent first and second substantially parallel sections of tissue, wherein the first set of needles are oppositely oriented to the second set of needles, and wherein first portions of a set of sutures are respectively coupled to the first set of needles, and second portions of the set of sutures are respectively coupled to the second set of needles;
    deploying the first and second sets of needles, such that the first set of needles, along with the first portions of the set of sutures, pass through the first section of tissue and exit at a first set of exit points, and the second set of needles, along with the second portions of the set of sutures, pass through the second section of tissue and exit at a second set of exit points;

retracting the first and second sets of needles through the respective first and second set of exit points, such that the first portions of the set of sutures decouple from the first set of needles and, after retracting the first set of needles, extend through the first set of exit points, and the second portions of the set of sutures decouple from the second set of needles and, after retracting the second set of needles, extend through the second set of exit points; and tensioning the set of sutures to suture the first and second sections of tissue together.

13. The method of claim 12, wherein the first and second sections of tissue form a tissue cuff.

14. The method of claim 13, wherein the tissue cuff includes a separated vaginal cuff, the first section of tissue is an anterior section of the separated vaginal cuff, and the second section of tissue is a posterior section of the separated vaginal cuff.

15. The method of claim 12, wherein a first set of anchors are respectively coupled to the first portions of the set of sutures and to the first set of needles, and a second set of anchors are respectively coupled to the second portions of the set of sutures and to the second set of needles;

wherein the first and second sets of needles are deployed, such that the first set of needles, along with the first set of anchors, pass through the first section of tissue and exit at the first set of exit points, and the second set of needles, along with the second set of anchors, pass through the second section of tissue and exit at the second set of exit points;

wherein the first and second sets of needles are retracted from between the first and second sections of tissue, such that the first set of anchors decouple from the first set of needles and, after retracting the first set of needles, extend through the first set of exit points, and the second set of anchors decouple from the second set of needles and, after retracting the second set of needles, extend through the second set of exit points; and wherein tensioning the set of sutures includes respectively advancing the first set of anchors along the set of sutures towards the second set of anchors to force the first and second sections of tissue together.

16. The method of claim 15, wherein the first set of anchors are slidably coupled to the first portions of the set of sutures, such that free ends of the set of sutures are free floating on one side of the first set of anchors, and the second set of anchors are fixedly coupled to the second portions of the set of sutures, wherein tensioning the set of sutures includes pulling on the free ends of the set of sutures, such that the first set of anchors are advanced along the set of sutures towards the second set of anchors to force the first and second sections of tissue together.

17. The method of claim 15, wherein the needles of the first set of needles respectively include a first set of apertures in which the first set of anchors are respectively positioned, and the needles of the second set of needles respectively include a second set of apertures in which the second set of anchors are respectively positioned.

18. The method of claim 1, wherein each needle of the first and second sets of needles is a curved needle, wherein deploying the first and second sets of curved needles includes rotating the first set of curved needles in a first direction about a first axis, and wherein rotating the second set of curved needles in a second direction, opposite to the first direction, about a second axis.

19. The method of claim 18, wherein retracting the first and second sets of curved needles includes rotating the first set of curved needles in the second direction about the first axis, and rotating the second set of curved needles in the first direction about the second axis.

20. The method of claim 18, wherein each curved needle of the first and second sets of needles is an arcuate needle.

* * * * *